(12) United States Patent
Baba et al.

(10) Patent No.: US 6,725,088 B2
(45) Date of Patent: Apr. 20, 2004

(54) FEMALE PHYSICAL CONDITION MANAGING APPARATUS

(75) Inventors: Michiko Baba, Shiraoka (JP); Kazue Sato, Senboku (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/968,037

(22) Filed: Oct. 2, 2001

(65) Prior Publication Data

US 2003/0073923 A1 Apr. 17, 2003

(30) Foreign Application Priority Data

Oct. 2, 2000 (JP) ........................................ 2000-302752

(51) Int. Cl.$^7$ ................................................. A61B 5/05
(52) U.S. Cl. ........................................ 600/547; 600/551
(58) Field of Search ................................. 600/547, 551, 600/587, 591

(56) References Cited

U.S. PATENT DOCUMENTS

| 4,008,712 A | * | 2/1977 | Nyboer ........................ 600/547 |
| 5,137,028 A | | 8/1992 | Nishimura ................... 128/738 |
| 5,817,031 A | * | 10/1998 | Masuo et al. ................ 600/547 |
| 6,125,297 A | * | 9/2000 | Siconolfi ...................... 600/300 |
| 6,354,996 B1 | * | 3/2002 | Drinan et al. ................ 600/551 |
| 6,402,699 B1 | * | 6/2002 | Kodama et al. ............. 600/551 |
| 2001/0007055 A1 | * | 7/2001 | Fukuda ........................ 600/547 |

FOREIGN PATENT DOCUMENTS

| EP | 0 498 303 A | 8/1992 |
| JP | 63-35249 | 7/1988 |
| JP | 04-2254 | 1/1992 |
| JP | 04-72261 | 11/1992 |
| JP | 07-24093 | 6/1995 |
| JP | 10-80426 | 3/1998 |

* cited by examiner

Primary Examiner—Max F. Hindenburg
Assistant Examiner—Jonathan Foreman
(74) Attorney, Agent, or Firm—McDermott, Will & Emery

(57) ABSTRACT

Disclosed is a female physical condition managing apparatus comprising: a bioelectrical impedance-meter; a memory for storing the so determined values of bioelectrical impedance; a decision-making unit for making a decision about the physical or mental condition of a woman on the basis of the time series analysis, which is made on the variation of the determined values of bioelectrical impedance; and a display showing the physical or mental condition of the woman in the form of graphs. This permits women to realize quickly what physical or mental condition they are put in. The female physical condition includes the premenstrual syndrome.

8 Claims, 30 Drawing Sheets

July 24 , 2000   08:30

Today PMS!

| Swell level |  |
| Feeling |  |
| Body condition |  |
| Skin condition |  |
| Pheromone |  |

FIG. 2  woman A : variations of body temperature and values of BI between both feet (not modified with weight)

woman A : relation between weight and BI
(not modified with weight)

R: correlation coefficient representing the degree to which
two variables correlate.
Its value ranges from 0.0 to 1.0. As its value is getting
close to 1.0, two variables x and y converge toward
one and same (x=y for R=1). No correlation is found
for R=0.

woman A : relation between basal body temperature and weight-modified BI appearing between both feet R=correlation coefficient

FIG. 25
July 24 , 2000  08:30
Please step on the bioelectrical impedance meter.
FIG. 26
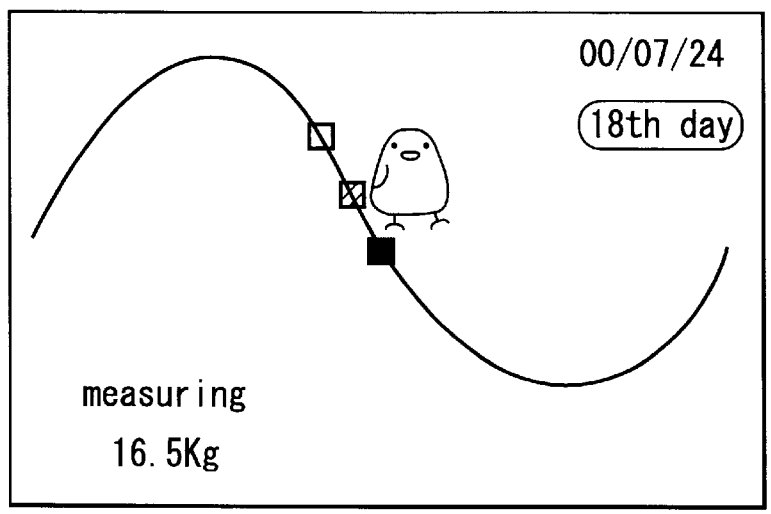
00/07/24
(18th day)
measuring
16.5Kg
FIG. 27
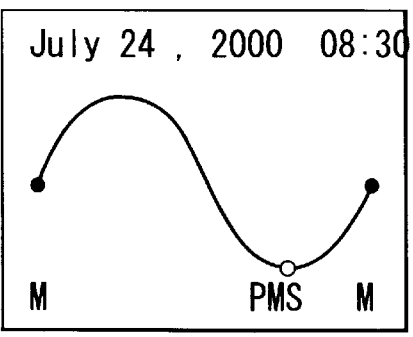
July 24 , 2000  08:30
M       PMS     M

FIG. 28

```
July 24, 2000   08:30
Today PMS!
  Swell level      ♦♦♦♦♦♦♦♦♦♦
  Feeling          ♥♥♡♡♡♡♡♡♡♡
  Body condition   ♥♥♥♡♡♡♡♡♡♡
  Skin condition   ♥♥♥♡♡♡♡♡♡♡
  Pheromone        ♥♥♡♡♡♡♡♡♡♡
```

FIG. 29

```
July 24, 2000   08:30
Today PMS!
─────────────────────────────
  Attention to elephant foot-like
  deformation.
  Vitamin and Kalium required.
  Cooked pumpkin recommendable.
  Drink mineral-rich water.
```

Pregnancy possibility suggested.
Better take pregnancy test.

| 28 day's cycle for averaging ▲ |
| average weight 50Kg          ▼ |

- ■ 6/24〜7/21···28 days' cycle  50Kg
- ■ 5/27〜6/23···28 days' cycle  51Kg
- ■ 4/29〜5/26···28 days' cycle  50Kg
- ■ 4/ 1 〜4/28···28 days' cycle  49Kg July 24, 2000
Probably tomorrow PMS!

Attention to elephant foot-like deformation.
Vitamin and Kalium required.
Cooked pumpkin recommendable.
Drink mineral-rich water.

FIG. 37

```
July , 24 (Monday)

any intimate        ······ ↑YES    ↓NO
contact ?

abnormal            ······ ↑YES    ↓NO
bleeding ?

menstruation        ······ ↑YES    ↓NO
period started ?
```

FIG. 38

```
July , 24 (Monday)

no intimate contact abnormal bleeding menstruation period started all correct ?              ↑ YES   ↓ NO
```

FIG. 39
```
July , 24 (Monday)
     no intimate contact
                                    
     abnormal bleeding
     menstruation period started
```
FIG. 40
```
June, 24 (Saturday)
        intimate contact
                                    
        no abnormal bleeding
        menstruation period not
        started
```

What do you want to know ?

↑↓ Date Day

FEMALE PHYSICAL CONDITION MANAGING APPARATUS

BACKGROUND OF THE INVENTION

1. Field of the Invention

The present invention relates to a female physical condition managing apparatus which is capable of making a decision about the female physical condition which appears periodically in a female, for example, on the ovulation day, at the time of appearance of the premenstrual syndrome (hereinafter abbreviated as "PMS") for menstruation period or for the pregnancy-possible period.

2. Prior Art

The women's periodic body condition is related closely with their body temperature. The body temperature transfers from the low-temperature period to the high-temperature period on the ovulation day, and from the high-temperature period to the low-temperature period on the menstruation starting day, as shown in FIG. 1. Women take their body temperature every morning in bed to make manually a graphic record or table showing how the body temperature varies each and every day, thereby making it possible to determine which stage has been reached in the periodic physical condition.

It is necessary that women take their body temperature while laying themselves in bed, and it takes them about five minutes to measure their body temperature with body thermometers. This, however, is difficult to continue for a long time, and women often fall in sleep while taking their body temperature in bed.

A reliable decision can be made about some particular types of female physical condition on the basis of the body temperature, such as determination of the ovulation day, the menstruation period and the pregnancy-possible period, all of which are useful factors for birth control. Determination about whether women undergo the PMS has been increasingly in concern from the point of women's daily life, but such decision is impossible with recourse to the recording of body temperature. The PMS starts seven days earlier than the beginning of the menstruation period, causing women to suffer from headache, irritation, stomachache, swell or any other unpleasing symptom. When they realize that their unpleasing symptoms are caused simply by the PMS, they can be released from their sufferings significantly.

As a matter of fact determination of the female physical condition from the graphic record of body temperature is difficult, and such determination is apt to be dependent on her discretion.

SUMMARY OF THE INVENTION

One object of the present invention is to provide a female physical condition managing apparatus which provides a quick decision on the periodic physical condition including the PMS.

To attain this object a female physical condition managing apparatus according to the present invention comprises: a bioelectrical impedance-meter for determining value of bioelectrical impedance; a memory for storing the so determined values of bioelectrical impedance; a decision-making unit for making a decision about the physical or mental condition of a female on the basis of the time series analysis made on the variation of determined values of bioelectrical impedance; and a display showing the physical or mental condition of the female in the form of graphs. Hereinafter, the word, "bioelectrical impedance" is abbreviated as "BI".

The mental condition includes at least one of the feeling, the skin condition and the emission of pheromone whereas the physical condition includes at least one of the swell and the body condition.

The graphs may include bar graphs, circle graphs, line graphs and radar charts.

The bar graphs, circle graphs, line graphs and radar charts may be given in two- or three-dimensional form.

Other objects and advantages of the present invention will be understood from the following description of some preferred embodiments of the present invention.

BRIEF DESCRIPTION OF DRAWINGS

FIG. 25 shows one example of a message describing what the user is requested to do at the start of a required measurement;

FIG. 26 illustrates a screen appearing in the display during the measurement;

FIG. 27 illustrates how the display indicates a decision made on the physical condition;

FIG. 28 illustrates how the cyclic messages are given in the display;

FIG. 29 shows the advice messages appealing in the display;

FIG. 30 shows a message informing the user of pregnancy possibility in the display;

FIG. 31 illustrates how the measurement results of weight and percent fat are shown in the display;

FIG. 32 shows the 28 days' cycle measurements of weight and percent fat;

FIG. 37 shows some items to be selected in logging a diary;

FIG. 38 shows the selected items for confirmation;

FIG. 39 shows the diary content of the day in question;

FIG. 40 shows the diary content of the day in question in the previous month;

DESCRIPTION OF THE PREFERRED EMBODIMENTS

Before entering the description of a female physical condition managing apparatus according to the present invention the relation between the BI and the women's periodic physical condition is described by referring to the data of actual measurement. Women took their body temperatures every morning when getting up, and the values of BI were measured between both feet.

Figure 1:
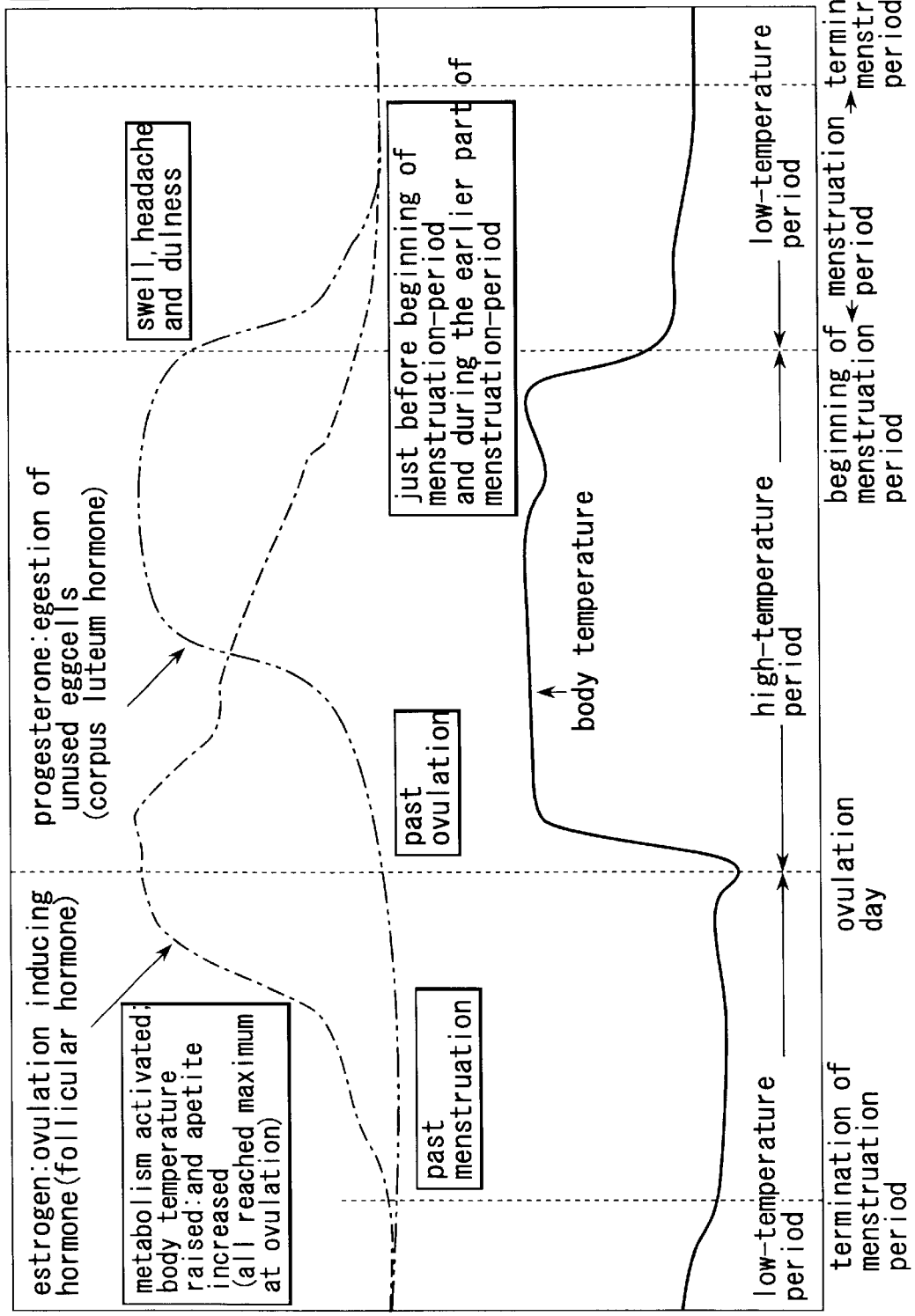
FIG. 1 shows how the monthly periodic physical condition of women, the body temperature and the secretion of hormone are related with each other.
Figure 2:
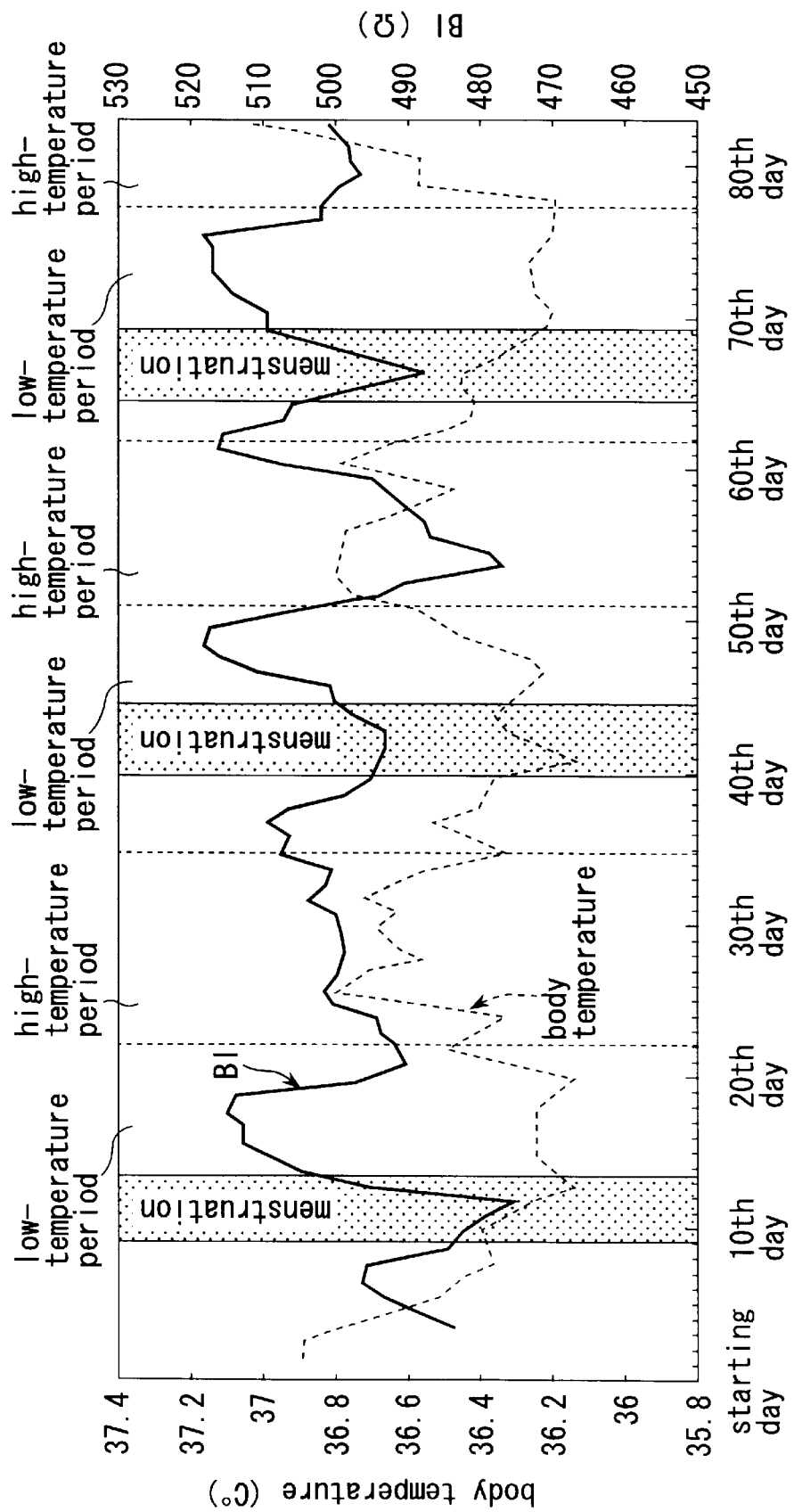
FIG. 2 illustrates how the body temperature and BI vary with day.

First, described is the periodic BI variation. FIG. 2 shows how the body temperature and BI of a selected woman A vary with day. The graphs were made by plotting the average values of two adjacent ones, which average values were determined according to the method of moving average. As a general tendency the values of BI remain high while the body temperature remains low. The values of BI remain low while the body temperature remains high, and the BI curve descends in the early half of the menstruation period after rising before the beginning of the menstruation period.

Figure 3:
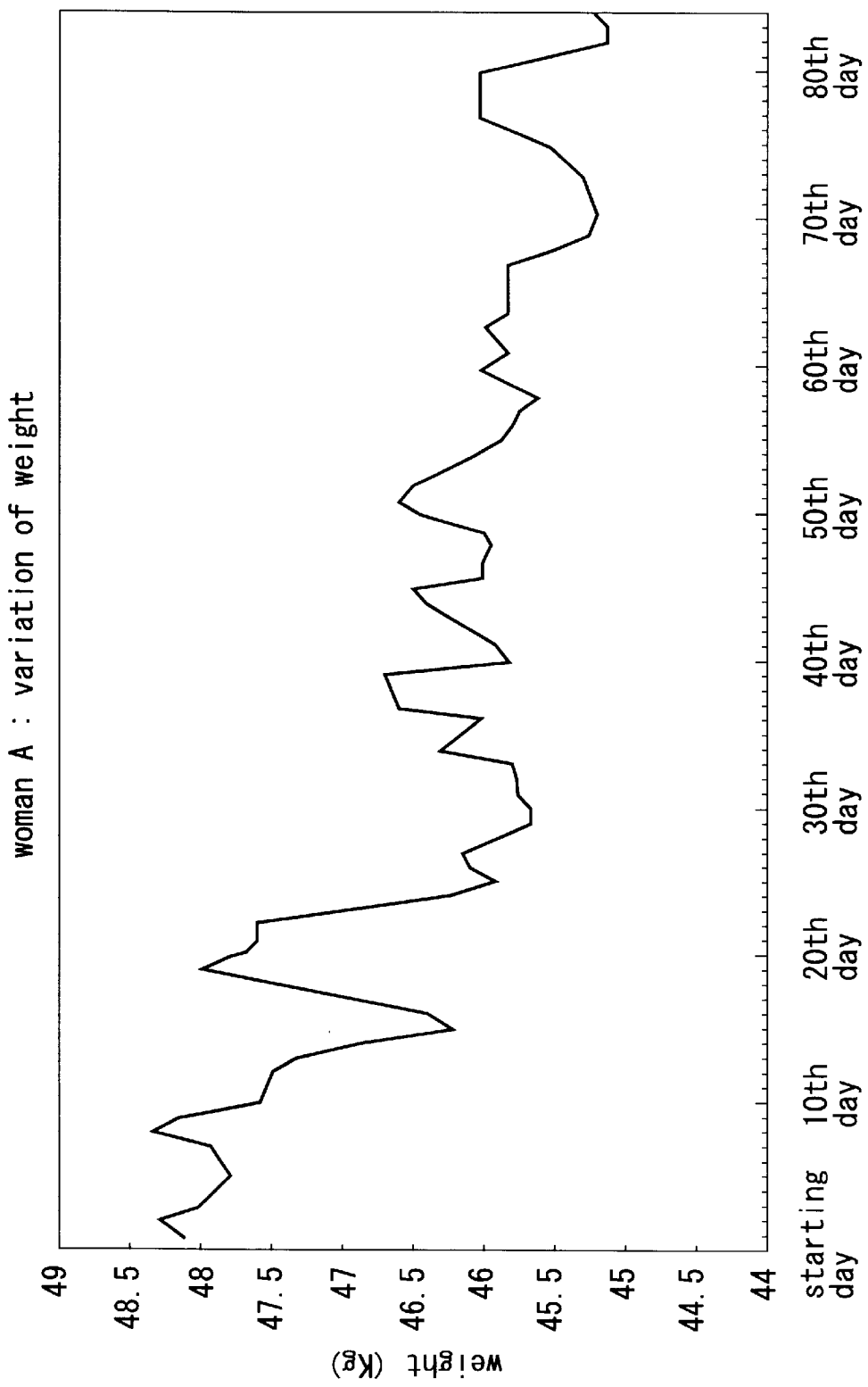
FIG. 3 illustrates how the weight varies with day.
Figure 4:
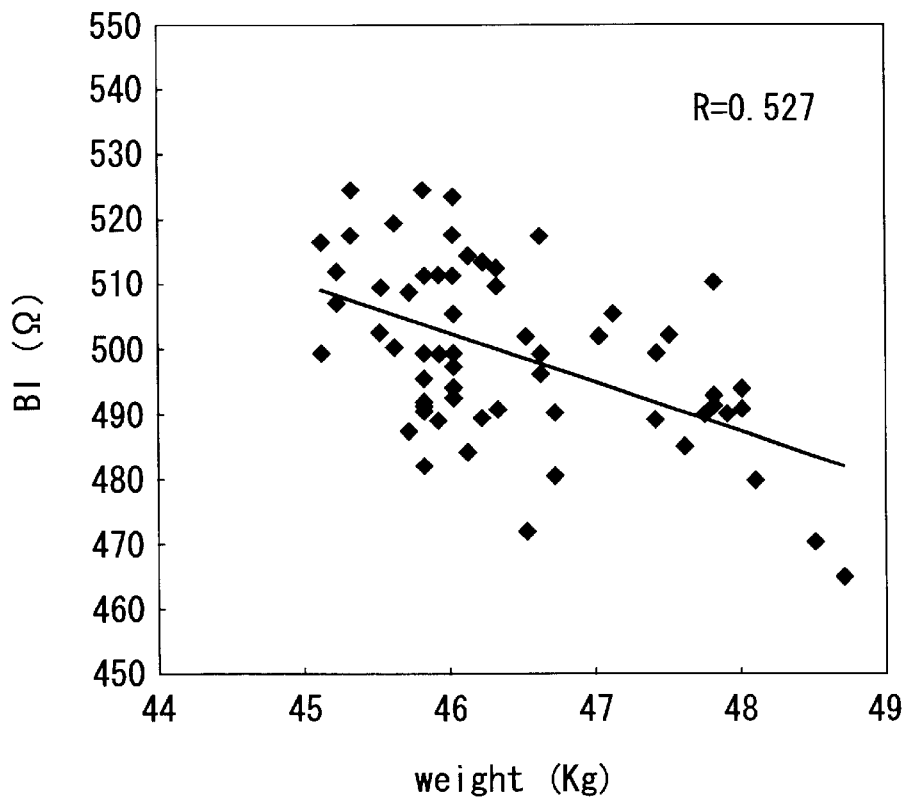
FIG. 4 illustrates how the weight and BI are correlated.

Next, the relation between the values of BI and the weight is described. FIG. 3 shows how the weight of the woman A varies while her physical condition was being monitored. The weight decreased gradually during measurement. FIG. 4 shows how the weight is correlated with the values of BI. A significant negative correlation between the weight and the values of BI was found (correlation coefficient R=0.527). As shown, the weight decreases with the increase of the values of BI, and vice versa. This inclination appears to be attributable to the fact that the water content of the female body increases (decreases) with the increase (decrease) of the weight and the value of BI decreases (increases) with the increase (decrease) of the water content. It appears that the BI curve of FIG. 2 is affected by the decreasing weight of the woman A as shown in FIG. 3 and that the BI curve needs to be corrected by modifying the values of BI with weight.

Figure 5:
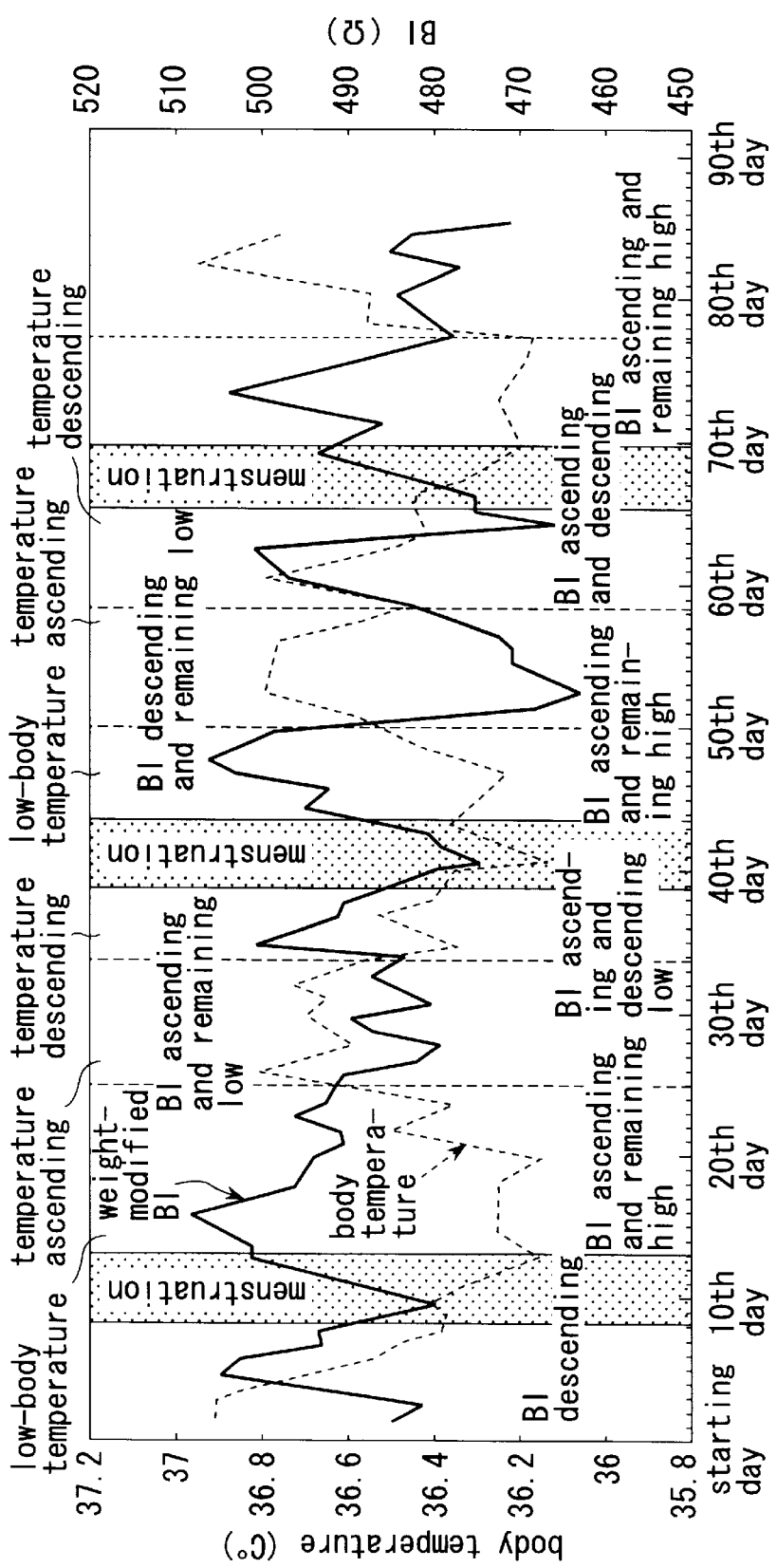
FIG. 5 illustrates how the weight-modified BI varies with day.

FIG. 5 shows the weight-modified BI curve, so that it may be made independent from the weight variation. Specifically the BI curve of FIG. 2 is modified according to Equation of Correction 1 or 2:

$$BI \text{ modified with weight} = BI + A \times (\text{difference of weight from the initial weight}) \quad (1),$$

or $$BI \text{ modified with weight} = BI + B \times (\text{difference of weight from the preceding weight}) \quad (2),$$

where "A" and "B" stand for correction coefficients.

The weight-modified BI curve of FIG. 5 shows the periodic variation of BI more clearly than the BI curve of FIG. 2, which is affected more or less by the variation of the weight.

Figure 6:
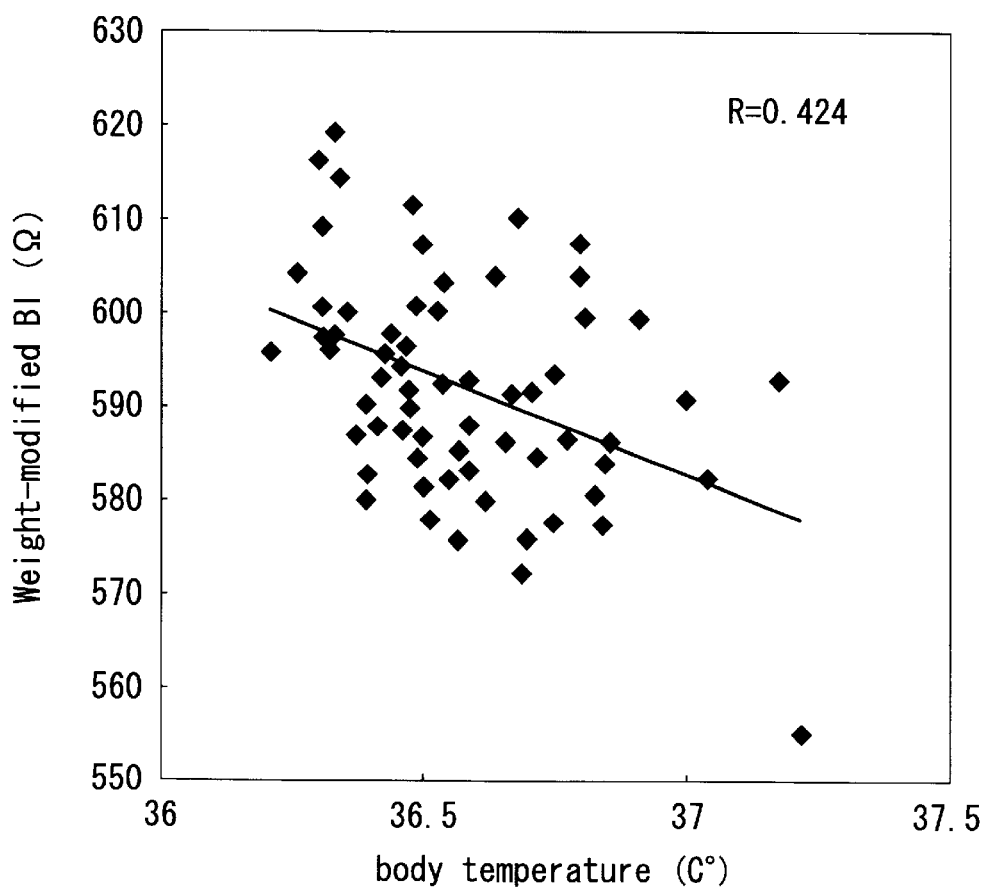
FIG. 6 illustrates how the weight-modified BI and the body temperature are correlated.

Next, the BI-to-body temperature relationship and the BI-to-PMS relationship are described. As seen from FIGS. 2 and 5, the values of BI decrease for a specific period spanning from the proximity to the menstruation beginning to the end of the early half of the menstruation period, for which specific period the body temperature decreases, too. Except for the specific period the values of BI remain high while the body temperature remains low. Because of this inconsistency there is little significant correlation between the body temperature and the values of weight-modified BI (correlation coefficient R=0.424) as shown in FIG. 6.

The decending of BI curve for the specific period (the body temperature descending) appears to be attributable to the swell of women's bodies; the water content of women's body is so high that the BI value may decrease significantly. Thus viewed, the values of BI and the swell are related as follows: as the swell appears, the values of BI decrease, and as the swell disappears, the values of BI increase. This suggests that a decision as to whether the swell appears in women's bodies can be made in terms of the values of BI. Apparently such a decision is impossible on the basis of the variation of body temperature. It is well known that appearance of the swell prior to the menstruation period is closely related with the PMS. Specifically the PMS accompanies the swell in women's bodies, and the PMS is liable to get worse as the swell increases in size. This suggests that a decision as to whether the woman undergoes the PMS can be made on the basis of the variation of BI, as is the case with the swell.

Figure 7:
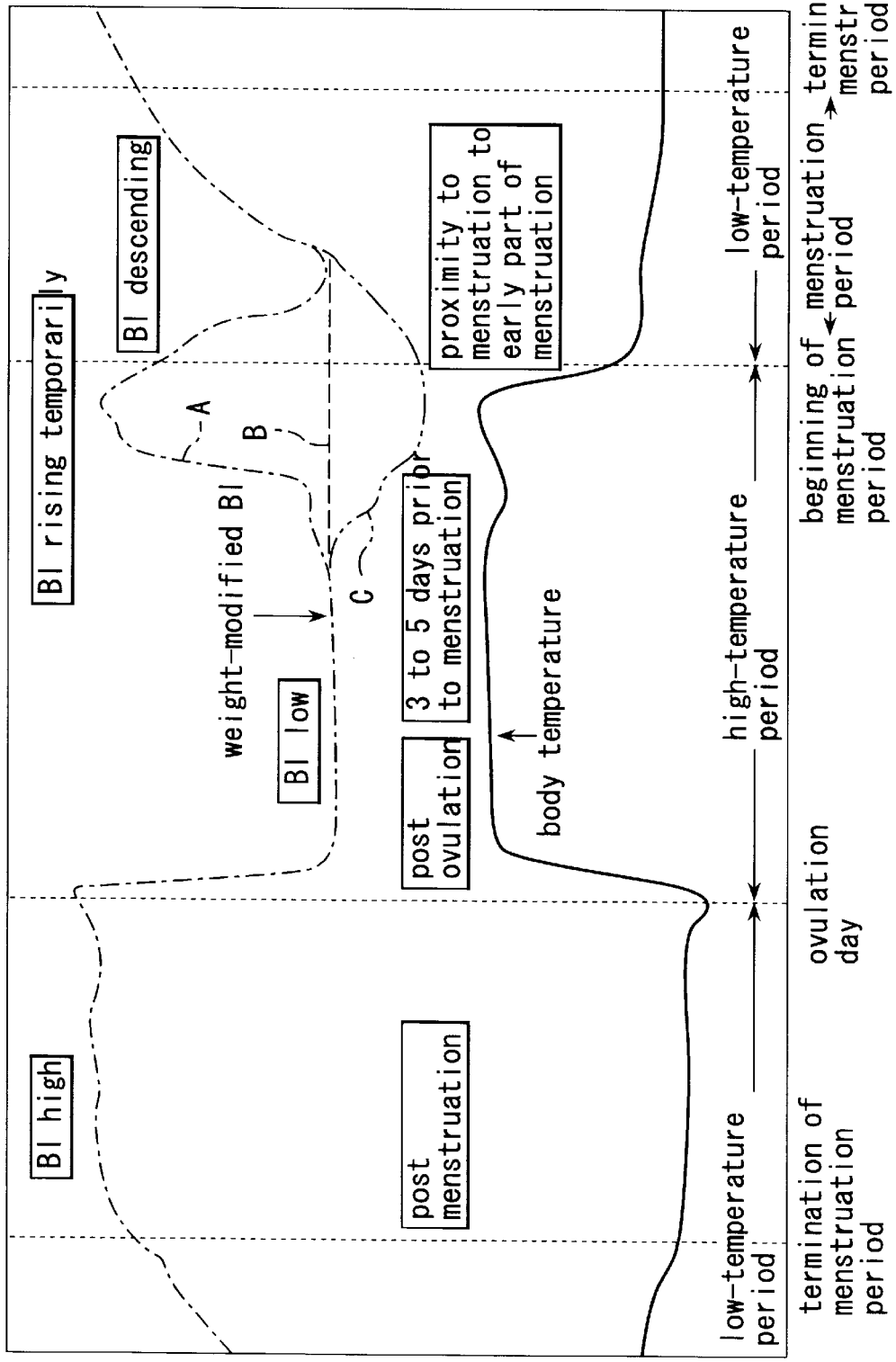
FIG. 7 illustrates how the weight-modified BI, the monthly periodic physical condition and the body temperature are related.
Figure 8:
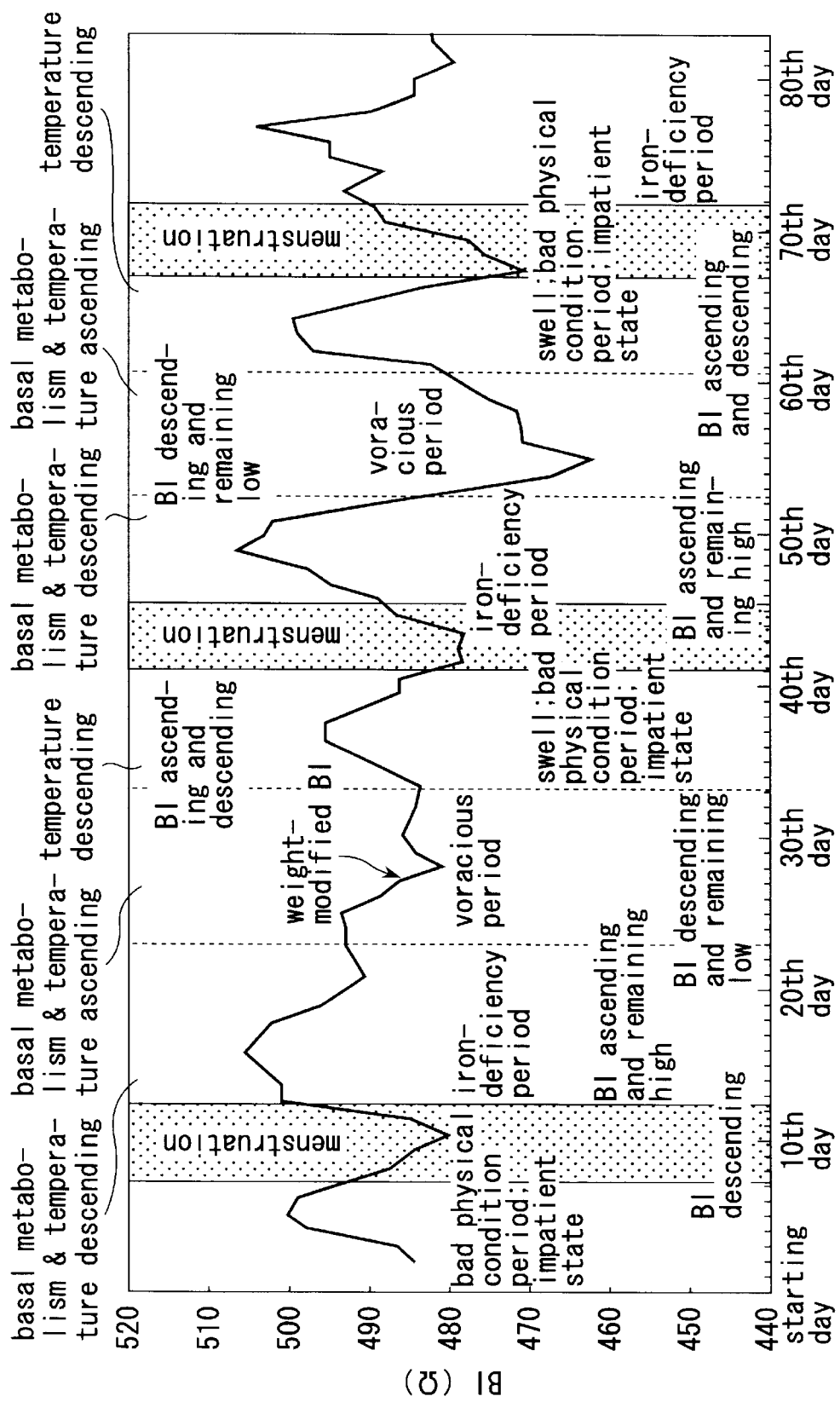
FIG. 8 illustrates how the weight-modified BI, the monthly periodic physical condition and the body temperature are related.

FIGS. 7 and 8 illustrate how the weight-modified values of BI and the body temperature are related with the monthly variation of female physical condition. These graphs show clearly that the BI curve is closely related with the monthly variation of female physical condition. This suggests that a decision on the monthly variation of female physical condition can be made on the basis of the BI curve, as for instance, follows: the ovulation day can be expected from the high-to-low transition of BI curve. Likewise, appearance of the swell or the PMS can be expected. Termination of the PMS can be decided from the rise of the BI curve. Also, termination of the menstruation period can be decided from the BI curve remaining stable at high level. There appear three different phases noticeable from the BI curve in the PMS-prevailing period. As seen from FIG. 7, the BI curve rises and falls just before the beginning of the menstruation period (noticeable from women of Type A). From the rise-and-fall of the BI curve it may be expected that this type of women undergo the PMS. The BI curve remains constant for women of Type B whereas the BI curve decreases for women of Type C. The descendent of the BI curve accompanies an irritation characteristic of PMS and appearance of the swell.

The values of BI were determined by measuring bioelectrical impedance appearing between woman's feet. The same results as described above were confirmed on so numerous women that the proposed method may be justly applied to diagnosis of women's periodical physical and mental condition. Measurement of bioelectrical impedance between both hands or one hand and one foot may be permitted, but measurement of bioelectrical impedance between both feet is most appropriate for the purpose because of the symptoms being clearly discernible from the BI curve provided by such inter-feet measurements.

Now, some embodiments of the present invention are described below with reference to drawings.

Figure 9:
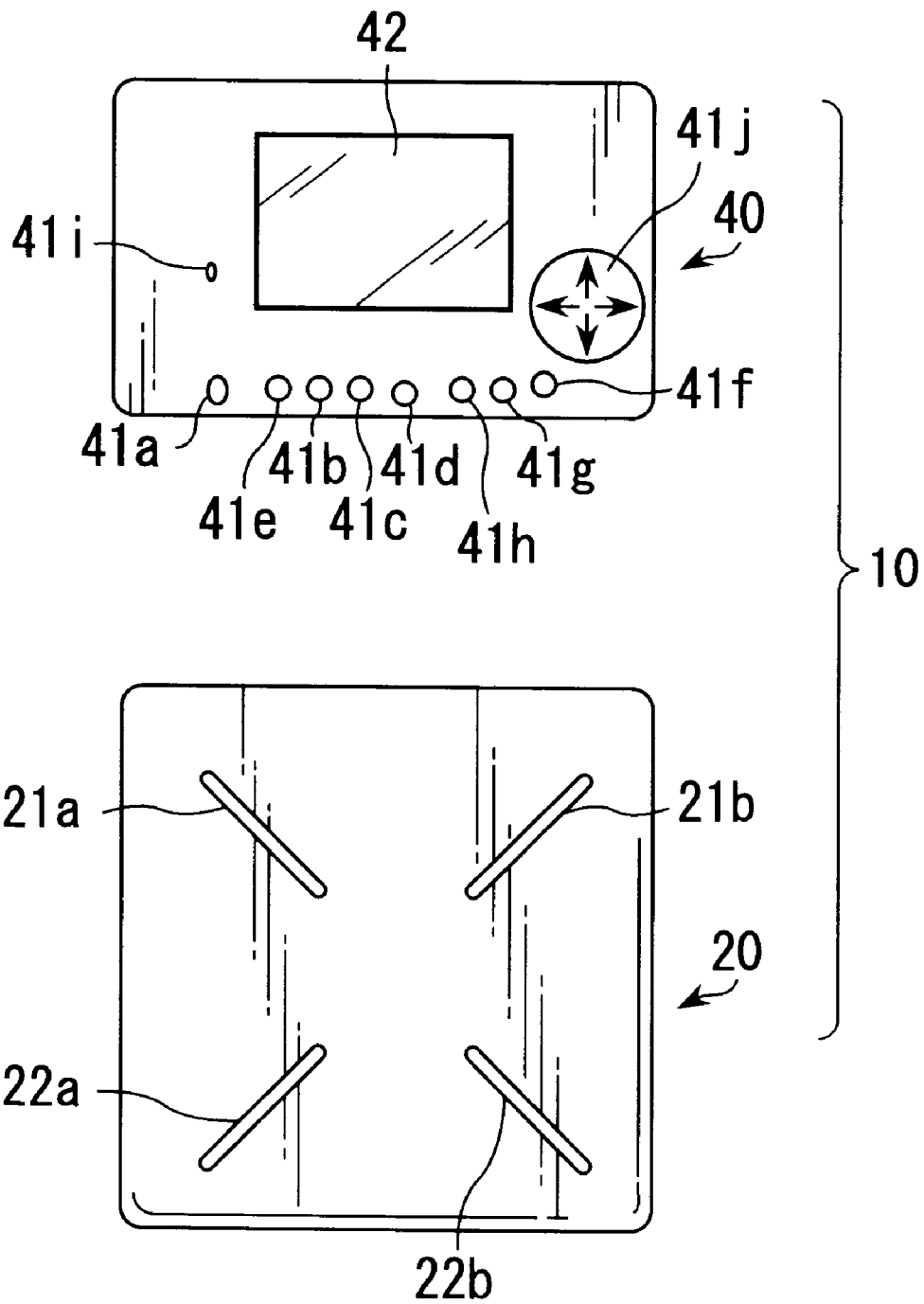
FIG. 9 illustrates how a female physical condition managing apparatus according to a first embodiment looks in appearance.

FIG. 9 shows the appearance of a female physical condition managing apparatus 10 according to a first embodiment. It comprises a scale-and-bioelectrical impedance meter 20 and a control box 40 connected to the scale-and-bioelectrical impedance via infrared or radio wave or via an electric cable. The scale-and-bioelectrical impedance meter 20 has constant current feeding electrodes 21a and 21b and voltage measuring electrodes 22a and 22b provided on its front side whereas the control box 40 has a group of operation buttons 41a to 41j and a display 42 provided on its front side. The group of operation buttons include a power source button 41a, a measurement button 41b, a registration button 41c, a transmission button 41d, a menstruation button 41e, a decision button 41f, a mode selection button 41g, a cancel button 41h, a reset button 41i and a direction button 41j. The direction button 41j has four button sector bearing directional indications →, ←, ↑ and ↓ thereon.

Figure 10:
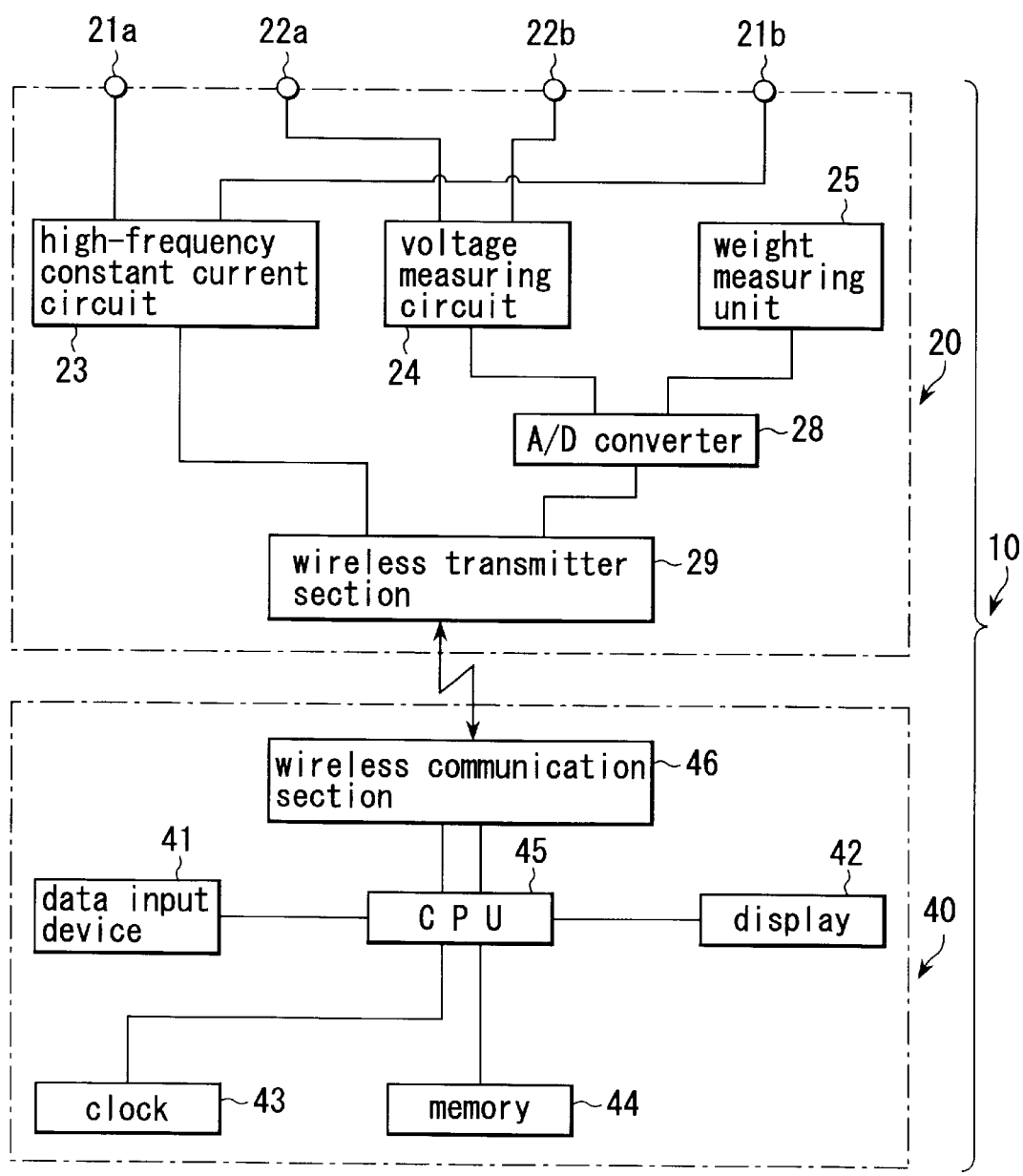
FIG. 10 is a block diagram showing the functions of the female physical condition managing apparatus.

FIG. 10 is a block diagram showing the functional structure of the female physical condition managing apparatus 10. The scale-and-bioelectrical impedance meter 20 comprises a high-frequency constant current circuit 23 for supplying a weak high-frequency constant current of fixed value to the constant current feeding electrodes 21a and 21b, a voltage measuring circuit 24 for measuring the voltage appearing between the voltage measuring electrodes 22a and 22b, a weight measuring unit 25, an A/D converter 28 for converting the measured voltage and weight to digital values and a wireless transmitter section 29.

In addition to the data-inputting buttons 41a to 41j and the display 42 for displaying the variation of BI, the determined physical condition and such like, the control box 40 comprises a clock 43 for showing on what day and time the measurement is effected, a memory 44 for storing the measured values of BI, the day and time at which measurements are effected, a CPU 45 for making a decision on the female physical condition on the basis of data pertaining to the menstruation period inputted by the data input device 41 and the measured values of BI, and a wireless communication section 46.

In this particular embodiment the scale-and-bioelectrical impedance meter 20 and the control box 40 make up the female physical condition managing apparatus. The scale-and-bioelectrical impedance meter 20 and the control box 40 may be combined as a whole.

Now, the manner in which the female physical condition managing apparatus works is described.

Figure 12:
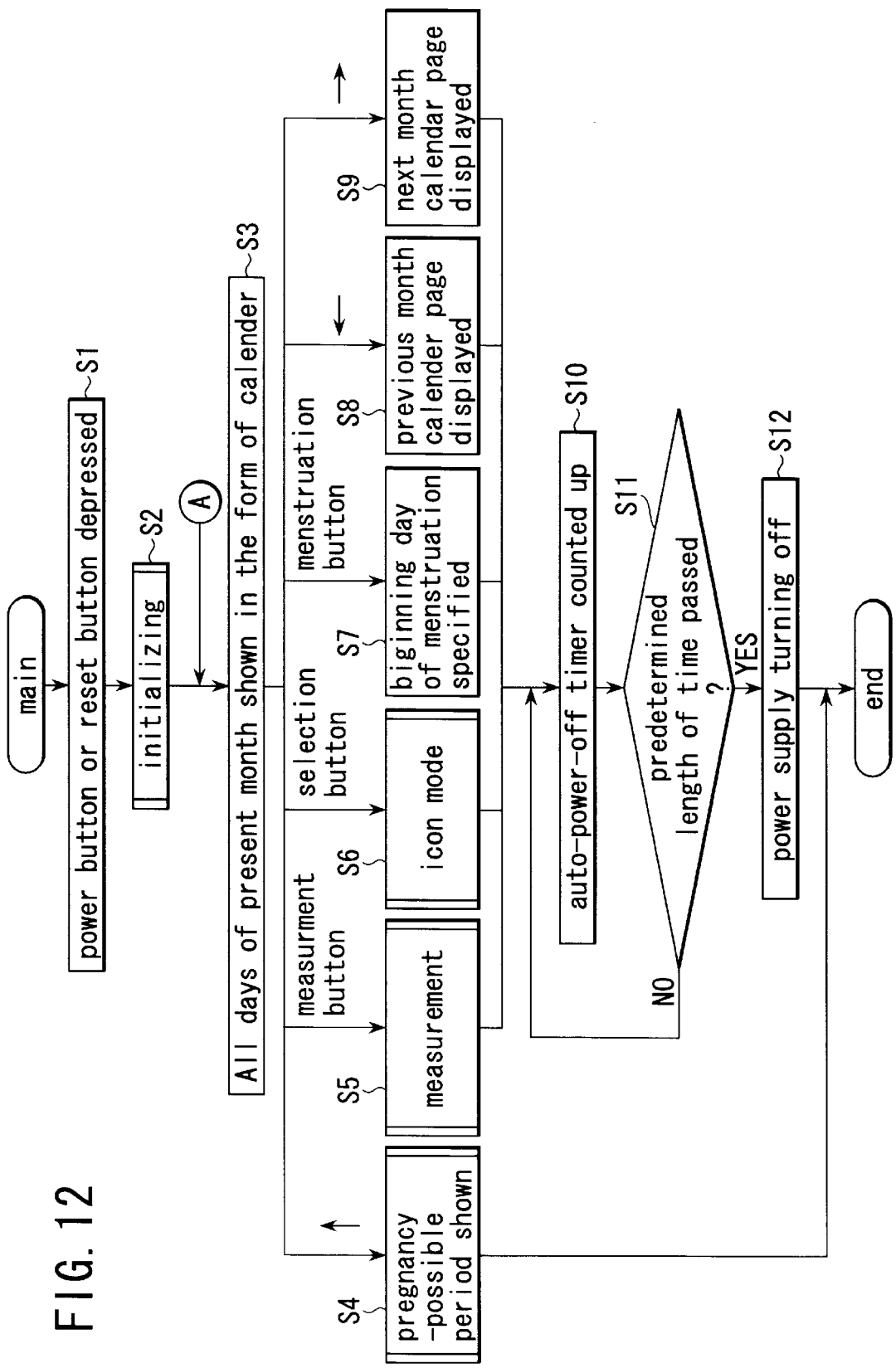
FIG. 12 is a flow chart showing the proceeding by which a decision is made on the monthly periodical physical condition.

FIGS. 12 to 18, 20 and 21 show the flowcharts describing the operation of the apparatus. FIG. 19 shows how selected phases of operation are shifted to each other by depressing selected operation buttons. First, referring to FIG. 12 showing the main program, the power button 41a is depressed at STEP S1, thereby putting the apparatus in circuit with the power supply. The apparatus is initialized at STEP S2 as later described in detail. All the days of the present month are shown in the form of calendar in the display 42 at STEP S3, as seen from FIG. 22. Different icons for commands appear on the heading of the screen. The figure 24 encircled with a rectangle represents the present day.

By depressing the button sector ↑ of the direction button 41j, the measurement button 41b, the selection button 41g, the menstruation button 41e or the button sector ← or → of the direction button 41j, S4, S5, S6, S7, S8 or S9 is executed, respectively.

At STEP S4 the apparatus works in the pregnancy-possible period presenting mode, thus displaying days corresponding to the expected start of the menstruation period and the possibility of pregnancy in the form of calendar. At STEP S5 the apparatus works in the measurement mode in which: the value of bioelectrical impedance and other factors are determined; and the results of the measurements are displayed. Some details are described later. At STEP S6 the apparatus works in the icon mode, in which any command selected by marking which one of the icons appearing in the calendar page may be executed. Some details are described later.

At STEP S7 the day of menstruation is specified on the calendar page. At STEP S8 the calendar page of the previous month appears on the screen. At STEP S9 the calendar page of the next month appears on the screen. At STEP S10 the auto-power-off timer is counted up. The timer permits disconnection from the power supply after the predetermined length of time has passed, and is reset in response to the turning-on of the power supply or to key depression. At STEP S11 a decision is made as to whether the predetermined length of time has passed. In the negative case the proceeding returns to STEP 10. At STEP S12 the power supply is made to turn off.

Figure 13:
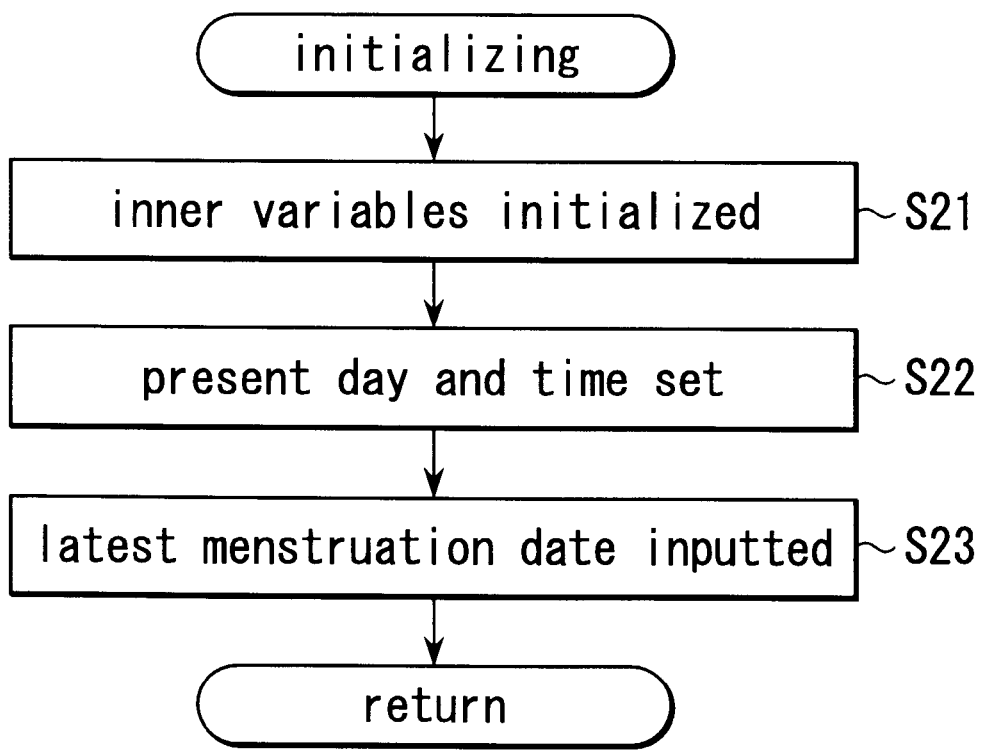
FIG. 13 is a flowchart according to which the initialization is performed.

Referring to FIG. 13, the initializing process (STEP S2) can start only when the power supply button is depressed for the first time or when the resetting button is depressed. A decision can be made as to whether the power supply has turned on before (in the affirmative case no initialization required); an initializing flag is set when the initialization has been completed, and therefore, at the first step it is necessary to check whether the flag has been set, and in the affirmative case no initialization is required.

At STEP S21 all inner variables are initialized. At STEP S22 the clock 43 is set for the present day and time. At STEP S23 the beginning day of the latest menstruation period or latest menstruation date is inputted.

Figure 14:
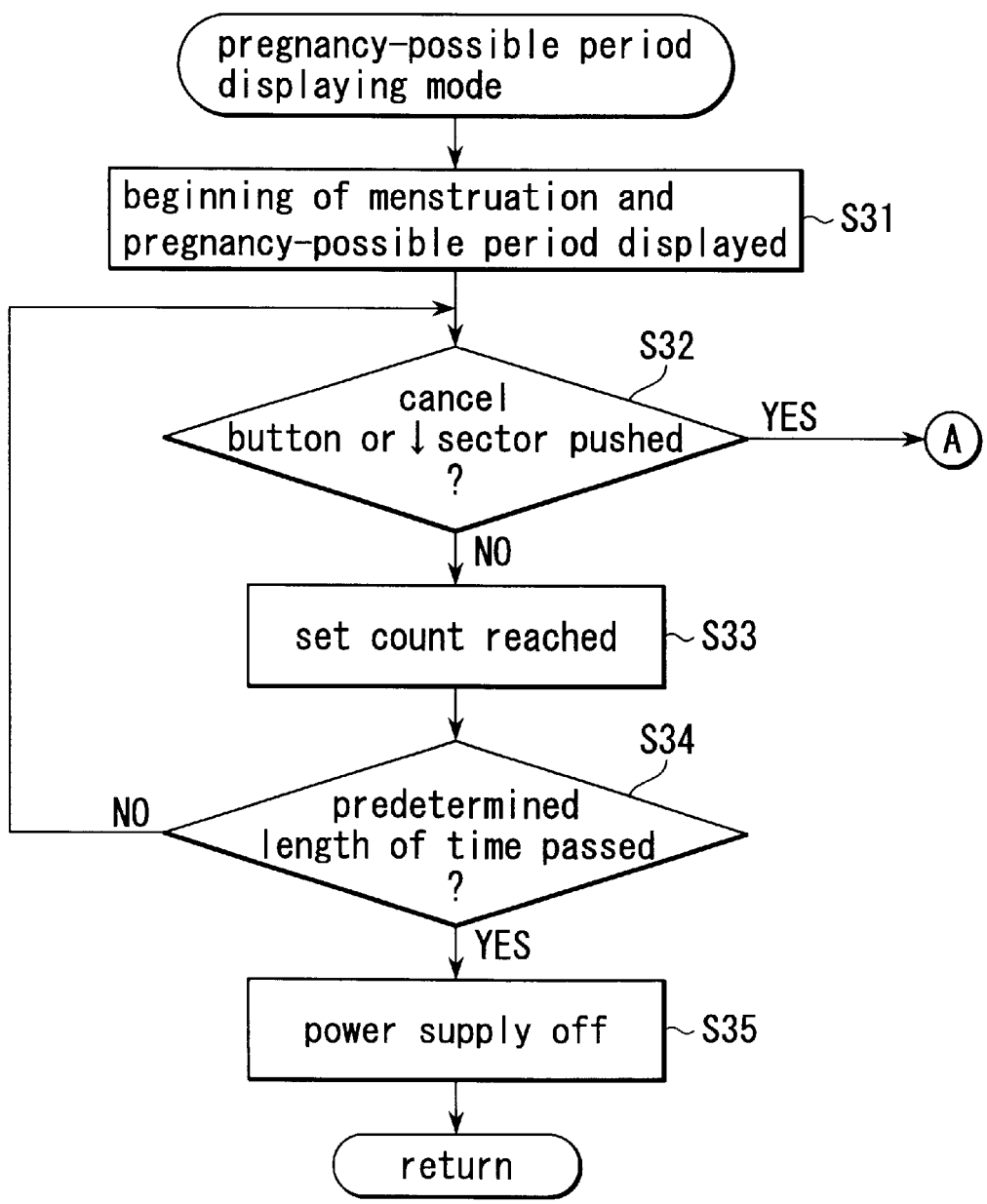
FIG. 14 is a flowchart showing the pregnancy-possible period presenting mode.
Figure 23:
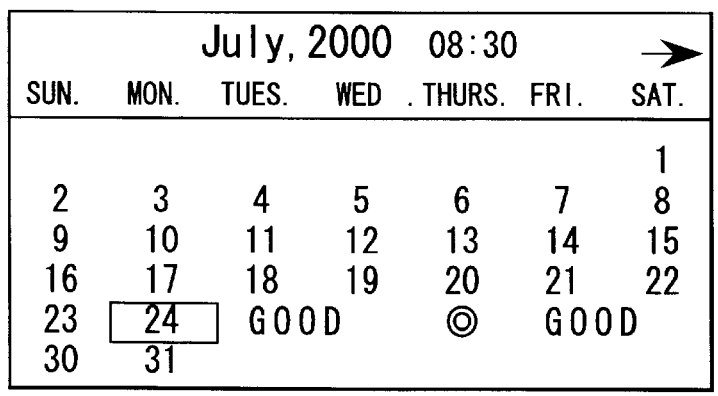
FIG. 23 illustrates how the pregnancy-possible day is indicated on a given page of the calendar.

Referring to FIG. 14, the pregnancy-possible period displaying mode (STEP S4) is described below. No corresponding icon appears in the screen because the relevant information needs to be kept confidential. At STEP S31 the pregnancy-possible period and the beginning day of the menstruation period (or beginning of menstruation) are shown on the screen, as seen from FIGS. 23 and 24. Specifically in FIG. 23 the ovulation day is indicated by a double circle ◎, and the words, "GOOD" sandwiching the double circle ◎ represent the pregnancy-possible period. The double-circle and the words appear alternately with the days hidden behind, blinking all the time. The Figure 24 encircled with a rectangle represents the present day.

Figure 24:
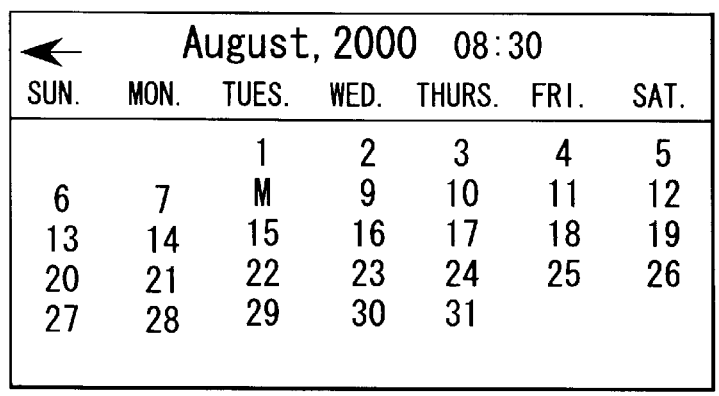
FIG. 24 illustrates how the expected beginning day of the menstruation period is indicated on a given page of the calendar.

Referring to FIG. 24, the expected menstruation beginning day is indicated by the letter M, and the letter and the expected day appear alternately, and blink. In a case where the pregnancy-possible period and the menstruation beginning day span two months, the arrow icon → blinks at the upper, right corner (see FIG. 23). The arrow button sector is depressed so that the next month calendar page appears (see FIG. 24). The next month calendar page has an arrow icon blinking on its upper left corner. In this example the pregnancy-possible period is five days long, including two days before and after the ovulation day. In another example the pregnancy possible period is determined to be nine days long, including the nineteenth to eleventh days counted backward from the day previous to the subsequent expected menstruation beginning day.

At STEP S32 a decision is made as to whether the cancel button 41h or ↓ button sector was pushed or not. In the affirmative the proceeding returns to the STEP S3, and then, the pregnancy-possible period presenting mode is finished. At STEP S33 the timer reaches the set count. At STEP S34 a decision is made as to whether the predetermined length of time has passed or not. In the negative the proceeding returns to STEP S32. In the affirmative the proceeding goes to STEP S35, where the power supply is disconnected.

Figure 15:
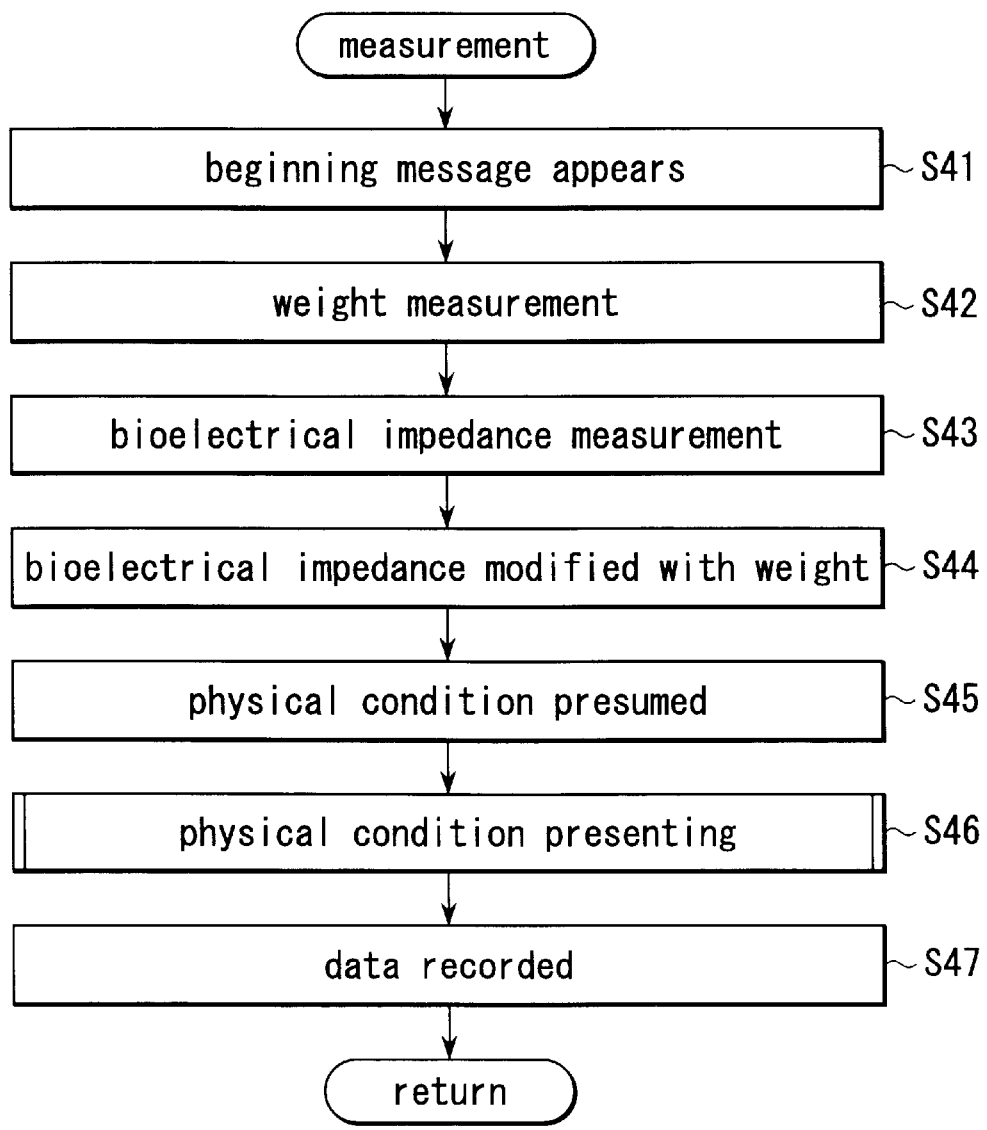
FIG. 15 is a flow chart according to which required measurements and estimations are made.

Referring to FIG. 15, the measurement processing (STEP 5) is described in detail. At STEP S41 a message reading "Please step on the bioelectrical impedance meter." appears and blinks in the display, as seen from FIG. 25. At the same time the date and time appear at the heading of the screen. When the cancel button 41h is pushed, the proceeding returns to STEP S3.

At STEP S42 the user stands on the bioelectrical impedance meter 20 equipped with the weight scale. Specifically she stands on the bioelectrical impedance meter with the toes and heels of the left and right feet put on the constant current feeding electrodes 21a and 21b and the voltage measuring electrodes 22a and 22b respectively. Now, the measurement starts with the weight of the user. At STEP S43 a high-frequency, constant current circuit 23 makes a high-frequency, weak current flow in her body via the constant current feeding electrode 21a, the toe of the left foot, the left leg, the lower part of her abdomen, the right leg, the toe of the right foot and the constant current feeding electrode 21b. A voltage measuring circuit 24 determines the voltage appearing between the voltage measuring electrodes 22a and 22b, thus determining the value of BI. The CPU 45 allows the display to show a sinusoidal wave of monthly-period curve as seen from FIG. 26. A chick character and a white square move on the sinusoidal curve back and force. A linear or circular curve may be used in place of the sinusoidal curve. The chick character may be replaced by another lovely animal shape. Some measurement data may be retrieved from the memory 44 to be shown by means of television opaque projector. This has the effect of releasing from the boring condition while waiting for the result. The white square □ may be replaced by the circle ○ or ●. The chick character may be changed in color or shape each and every month or day. The value of BI determined at STEP S44 is modified according to the weight-modification equation (1) or (2) as described above to provide the weight-modified BI value.

At STEP S45 the present physical condition is determined in consideration of the female physical condition-and-bioelectrical impedance relationship. The required determination can be made on the basis of the present weight-modified BI (which is determined at STEP S44), the previous weight-modified BI (which is retrieved from the memory 24) and data collected for the menstruation period as follows:

the menstruation beginning day has been specified at STEP 7 in FIG. 12, and is regarded as the beginning day of the menstruation period, and the week counted forward from the beginning day of the menstruation period is called "First Period" (menstruation period). The "Second Period" (Good Condition Period) spans from the day following the termination of the "First Period" to the day previous to the first day on which the BI value is measured to be 4% less than the average BI value of the Second Week of the previous monthly record. The "Third Period" (Steady Period) spans from the day following the termination of the "Second Period" to the day one week backward from the beginning day of next menstruation period, which beginning day is presumed to be from the history or past record of female physical condition. Finally, the "Fourth Period" (PMS period) spans from the day following the termination of the Third Period to the specified beginning day of the next menstruation period. Appearance of PMS can be determined by making a decision as to which type of graphic variation appears at the transition to the rise of BI curve, TYPE A, B or C (see FIG. 7). Specifically when the present physical condition is found to be of TYPE A, the appearance of PMS may be presumed. The ovulation day may be justly determined as falling on the fourteenth day counted backward from the beginning day of next menstruation period, which beginning day is determined from the past record of data. The ovulation day is the last day of the "Good Condition Period", and if the ovulation day should fall on the day following the last day, the pregnancy-possible day needs to be corrected accordingly.

The practice of a decision being made as described requires the past record of data, which was made at least one month previous to the decision making. In a case where no prior record is available, the message which reads "required data unavailable" appears in the display.

Now, the manner in which a decision is made as to whether the swell characteristic of PMS appears is described below. The average value of BI is determined from those recorded for a selected PMS period in the past, and the so determined average BI value is used as the STANDARD. Specifically the degree of swell is determined as SWELL LEVEL 1 when the BI value decreases 1% down with respect to the STANDARD, and the degree of swell rises one level high each time the BI value has decreased 1%

At STEP S46 the measurement and decision is completed to show the so decided physical condition in the display, as later described in detail. At STEP S47 the → button sector is depressed, or otherwise, the predetermined length of time has passed, and then, the message which reads "Push the record button to record the data." appears in the display. The record button 41c is pushed to store in the memory 44 the weight-modified BI value and the weight, both of which are determined this time. Then, the proceeding returns to the main program.

Figure 16:
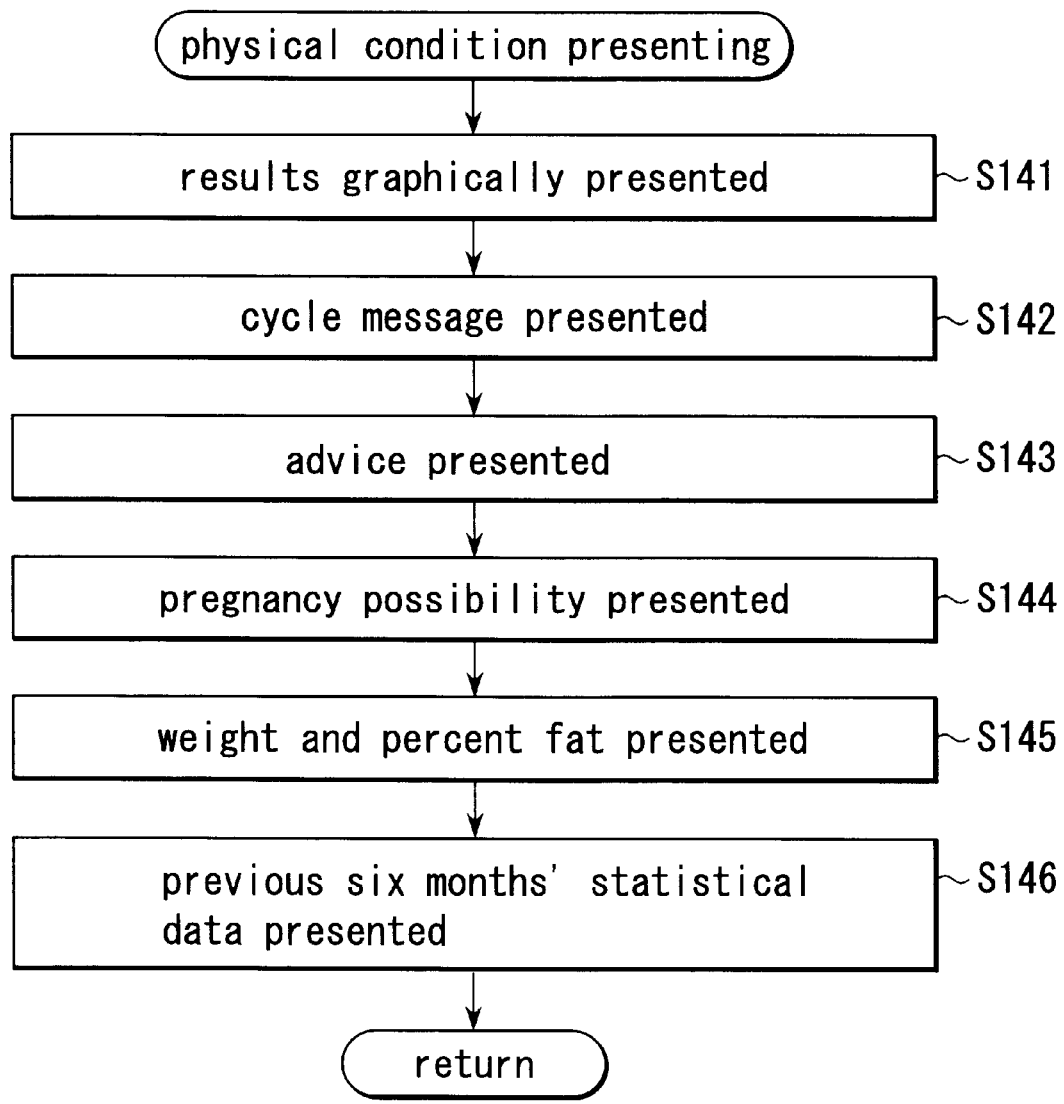
FIG. 16 is a flow chart showing a series of steps for displaying the physical condition.

Referring to FIG. 16, the physical condition presenting processing is described (STEP S46). Referring to FIG. 27, a circle ○ on the sinusoidal curve stays on the day on which the measurement is made, and it blinks there. At the same time, the message describing the present physical condition such as "PMS" appears and blinks, too. After a while the blinking stops, allowing the word to appear still. The letter "M" appearing at the lower left and right corners indicates the menstruation period. At STEP S142 the → button sector is depressed, or otherwise, the predetermined length of time has passed, and then, the message which describes the physical condition appears in the display, as shown in FIG. 28. The message contains "Swell level", "Feeling", "Body condition", "Skin condition" and "Pheromone". The "Swell level" is given by the number of reversed marks, each representing one level high. The levels of "Feeling", "Body condition", "Skin condition" and "Pheromone" in "First Period" (Menstruation Period) "Second Period" (Good Condition Period) and "Third Period" (Steady Period) are given in terms of the number of days counted from the beginning of each period. As for the PMS period the levels of "Feeling" and "Body condition" are determined from the swell level, which is determined from the variation of BI values as described at STEP S45. The increase of swell in size indicates the intracerebral edema. Then, the woman may be impatient, and the level of "Feeling" lowers. Also, she feels lassitude, and accordingly the "Body condition" remains at a low level. The "Pheromone" will increase to the maximum level (100%) on the ovulation day. In this particular example these mental or physical conditions are given in the form of bar graphs, but they may be given in the form of circular or line graph or in the form of radar chart. A three-dimensional presentation is possible. At STEP S143 the → button sector is depressed or otherwise, a predetermined length of time has passed, advisory messages in connection with the physical or mental condition are given, as seen from FIG. 29. At STEP S144 the → button sector is depressed or otherwise, a predetermined length of time has passed, and then, if a decision is made on the pregnancy possibility, the message is given in the display 42, as seen from FIG. 30. At STEP S145 the → button sector is depressed or otherwise, a predetermined length of time has passed. Then, the weight and the percent fat are given with indications (↑) and (↓), as seen from FIG. 31. At STEP S146 the → button sector is depressed or otherwise, a predetermined length of time has passed. Then, the display shows the average of the days included in the menstruation cycle each of the previous six months, the average the menstruation cycle beginning and ending days, the number of the days included in the weight, the menstruation cycle and the average weight for the menstruation cycle, all counted or calculated in selected menstruation cycles in the past.

Figure 17:
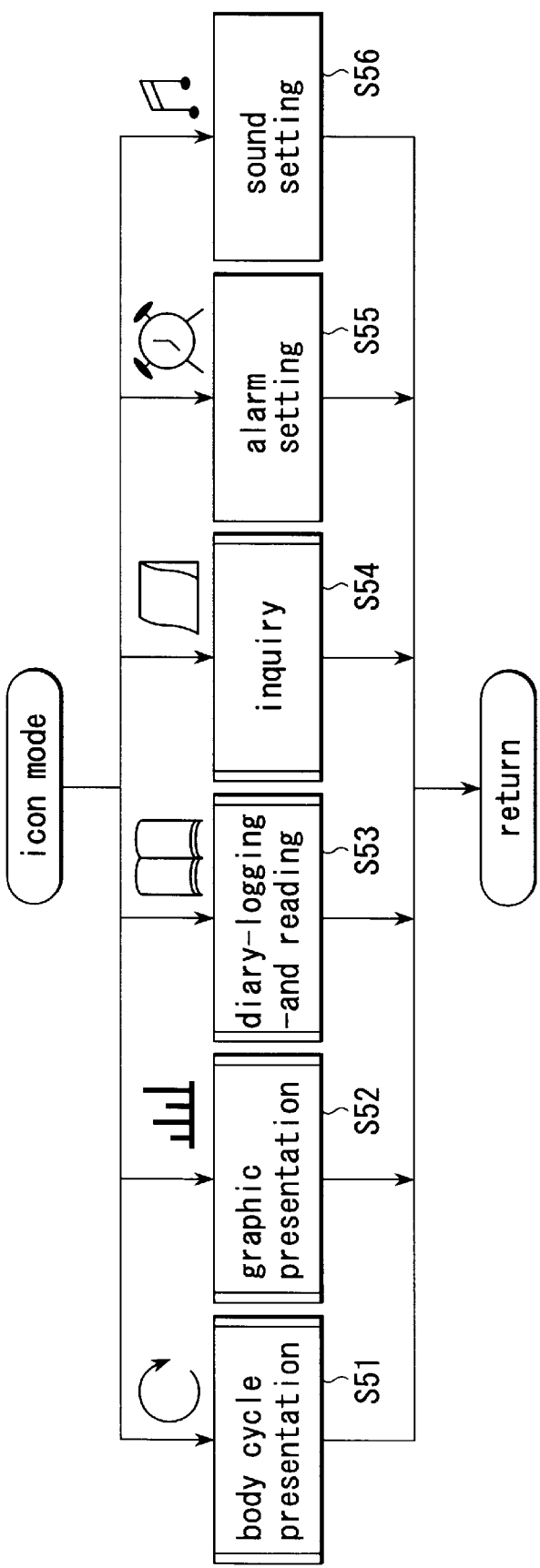
FIG. 17 shows what icons are displayed for selection.

Referring to FIG. 17, icon mode processing (at STEP S6) is described below. First, the body cycle icon (see the top of FIG. 22) is selected by the selection button 41g, and then the decision making button 41f is depressed, allowing the proceeding to advance to STEP S51, at which the processing of body cycle presentation is effected. The graphic presentation icon is selected by the selection button 41g, and then the decision making button 41f is depressed, thereby giving the graphic presentation in the display. The diary logging-and-reading icon is selected by the selection button 41g, and then the decision making button 41f is depressed, allowing the proceeding to advance to STEP S53, at which the diary logging-and-reading is permitted. Likewise, the inquiry icon is selected, and the decision making button 41f is depressed, thereby allowing the proceeding to advance to STEP S54, at which the inquiry is permitted. Now, the alarm setting icon is selected, and the decision making button 41f is depressed, so that the proceeding may advance to STEP S55, at which the required alarm setting is effected. By this processing, the date and time that are famous for alarm sound are set. The sound setting icon is selected by the selection button 41g, and then the decision making button 41f is depressed, thereby allowing the proceeding to advance to STEP S56, at which the sound setting is effected. The on-and-off operation for producing sound other than alarming sound can be set. Some details of each processing are described below by referring to FIGS. 18 to 21.

Figure 18:
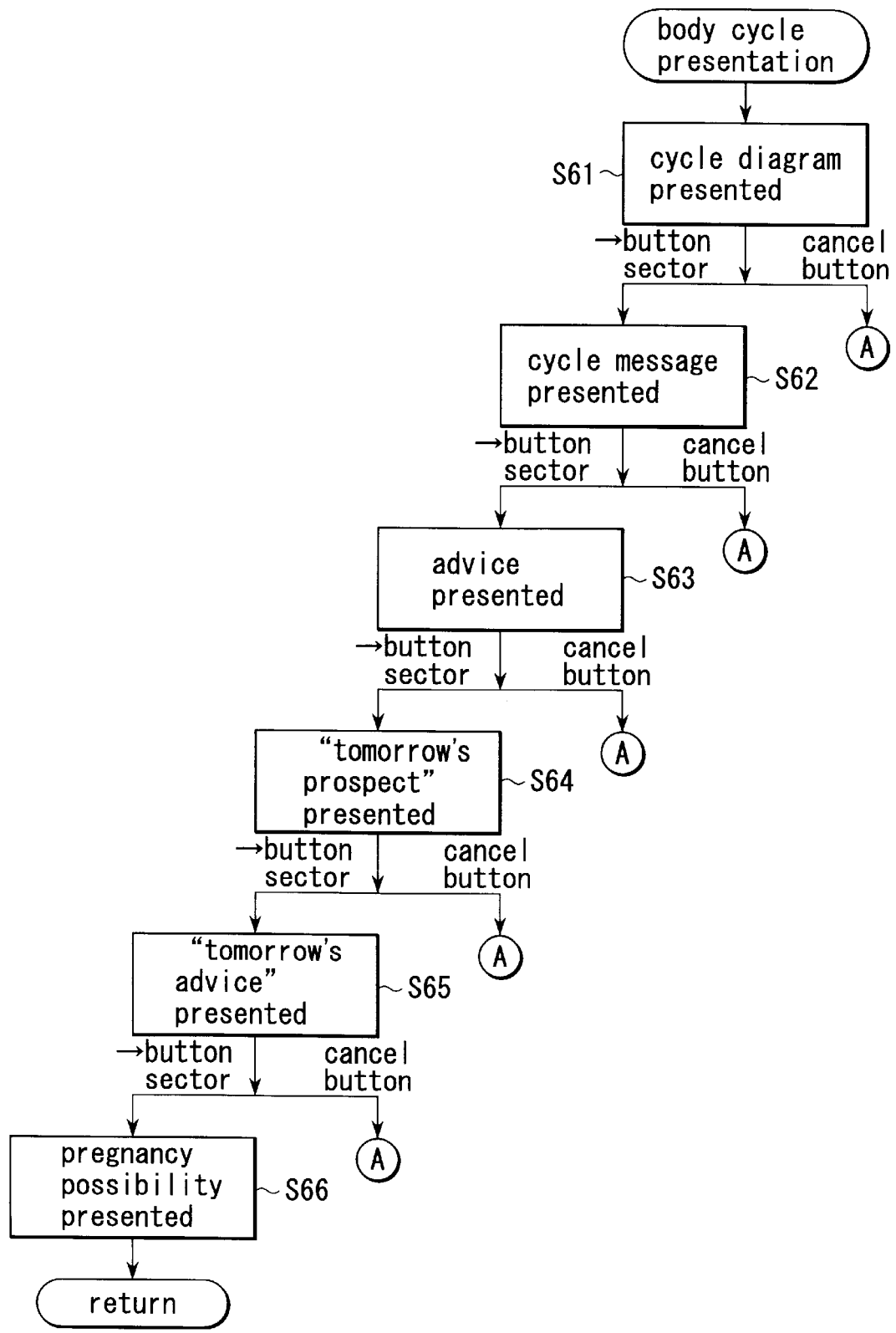
FIG. 18 is a flow chart showing the proceeding by which cyclic body conditions and related advice are given.
Figure 19:
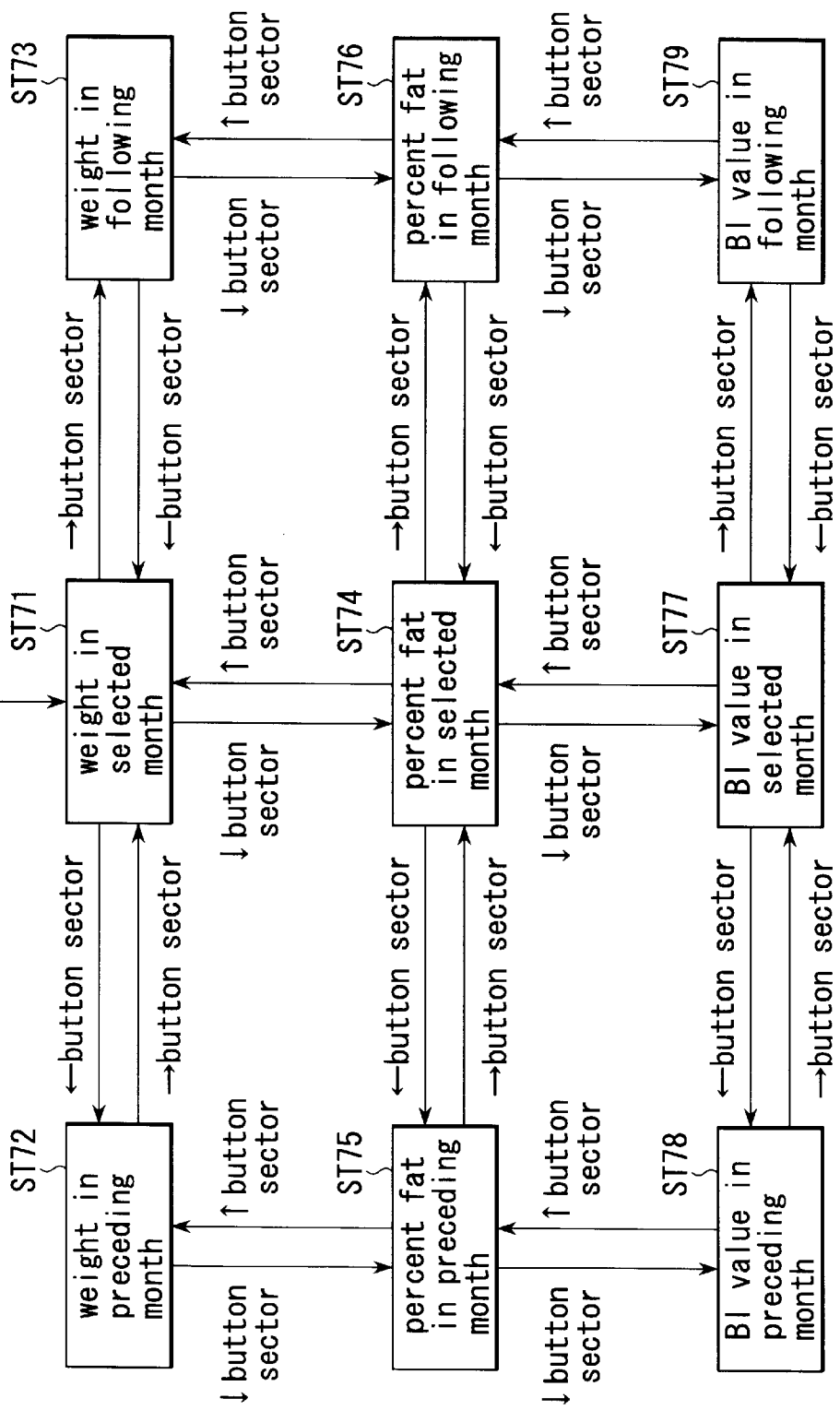
FIG. 19 shows how different items can be transferred from one to another in graphic presentation.
Figures 33, 34:
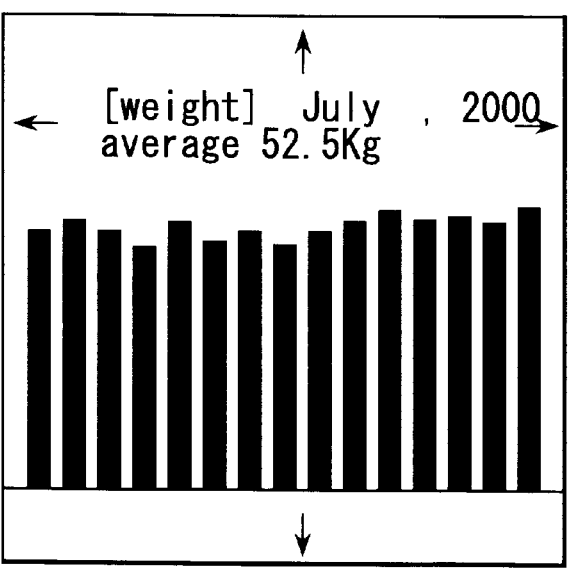
FIG. 33 shows one example of tomorrow's message in the display.
FIG. 34 shows how the weight varies within one month.
Figure 35:
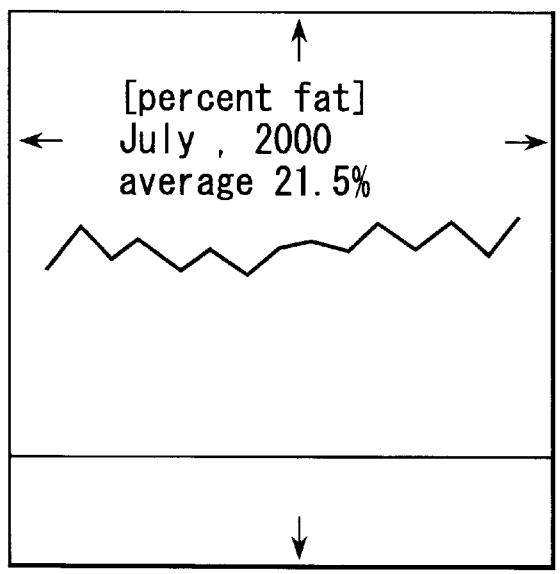
FIG. 35 illustrates how the percent fat varies within one month.
Figure 36:
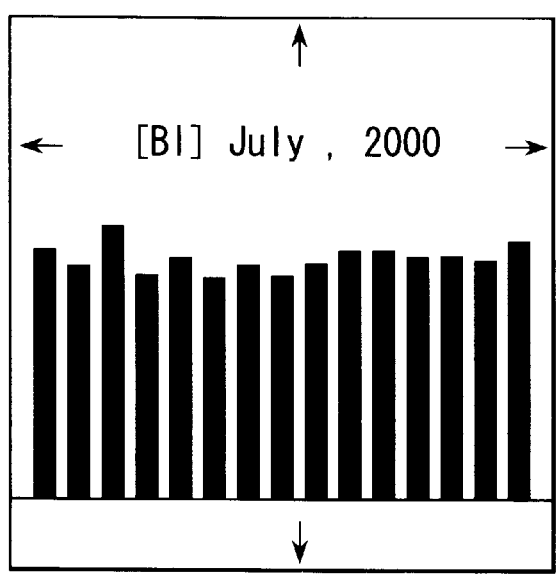
FIG. 36 illustrates how BI values vary within one month.

Referring to FIG. 18, the body cycle presentation processing (STEP S51) is described. The cyclic curve (see FIG. 27) appears as is the case with STEP S141 (see FIG. 16). When the cancel button is depressed, the proceeding returns to STEP S3. The → button sector is depressed or otherwise, a predetermined length of time has passed. As is the case with STEP S142, the cycle message appears (see FIG. 28) as described at STEP S142. Depression of the cancel button permits the proceeding to return to STEP S3. The → button sector is depressed or a predetermined length of time has passed. As is the case with STEP S143, advice messages (see FIG. 29) are given at STEP S63. Depression of the cancel button permits the proceeding to return to STEP S3. The → button sector is depressed or a predetermined length of time has passed. Then, the "Tomorrow's Prospect" message appears at STEP S64. Depression of the cancel button permits the proceeding to return to STEP S3. The → button sector is depressed or a predetermined length of time has passed. Then, the Tomorrow's Advice messages (FIG. 33) are given at STEP S65. Depression of the cancel button permits the proceeding to return to STEP S3. In a case where a decision is made on the pregnancy possibility, the → button sector is depressed or a predetermined length of time has passed. Then, the woman is informed of the possibility of being pregnant (FIG. 30) at STEP S66, as is the case with STEP S144.

Referring to FIG. 19, the graphic presentation processing (STEP S52) is described. The graph given in the STATE ST71 shows the variation of the weight in a selected month and the average weight (see FIG. 34). Depression of the ← button sector makes the presentation transfer to the STATE ST72, where the variation of the weight in the preceding month and the average weight are shown. Depression of the → button sector makes the presentation transfer to the STATE ST71. Other state transfers equally, too. In the STATE ST73 the variation of the weight in the following month and the average weight are shown. In the STATE ST74 the variation of the percent fat in the selected month and the average percent fat are shown. In the STATE ST75 the percent fat in the preceding month and the averagee percent fat are given. In the STATE ST76 the variation of the percent fat in the following month and the average value are given. In the STATE ST77 the graphic presentation of BI values in the selected month and the average value are given. In the STATE ST78 the graphic presentation of BI values in the preceding month and the average value are given. In the STATE ST79 the graphic presentation of BI values in the following month and the average value are given. A predetermined length of time has passed without depressing the → or ← button sector, and then, the power supply is made to turn off.

Figure 20:
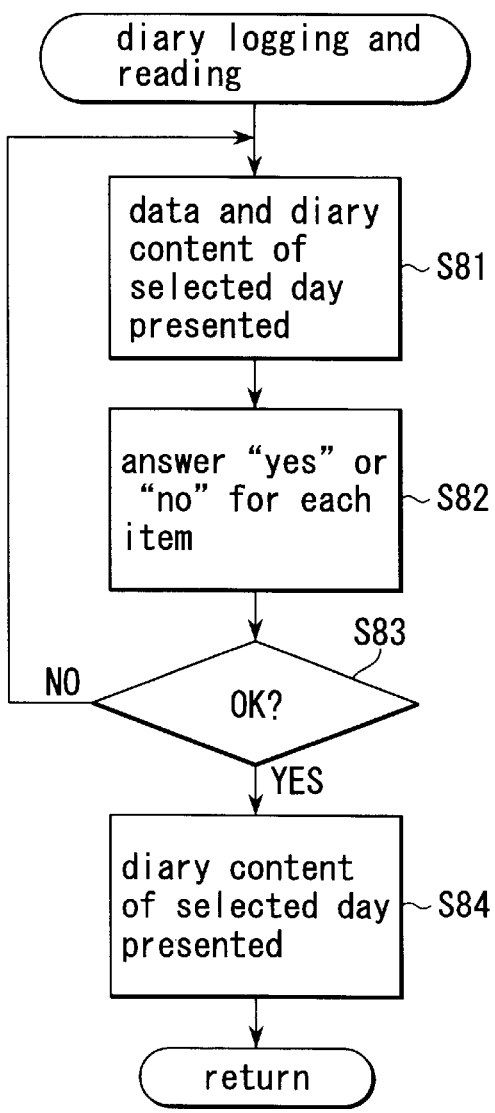
FIG. 20 is a flow chart showing the proceeding by which a diary is logged and read.

Referring to FIG. 20, the diary logging-and-reading processing (STEP S53) is described. At STEP S81 a selected date and the diary page of the selected date appear in the display 42, as seen from FIG. 37. At STEP S82 the woman answers each question by selecting YES or NO. In selecting YES the ↑ button sector is depressed, and then, the decision making button 41f is depressed. In selecting NO the ↓ button sector is depressed, and then, the decision making button 41f is depressed. Desired entry in the selected previous diary page (or backlogging) may be permitted by using the ← button sector. When the cancel button is depressed, the proceeding returns to STEP S3. At STEP S83 a confirmation screen appears, as seen from FIG. 38. The woman can say, "YES" or "NO" by pushing the ↑ button sector or ↓ button sector, and by pushing the decision making button 41f. When "NO" is selected, the proceeding returns to STEP S81. At STEP 84 the selected diary page appears (see FIG. 39). When the ← button sector is depressed, another selected diary page is shown (see FIG. 40). Depression of the → button sector makes the proceeding go back.

Figure 21:
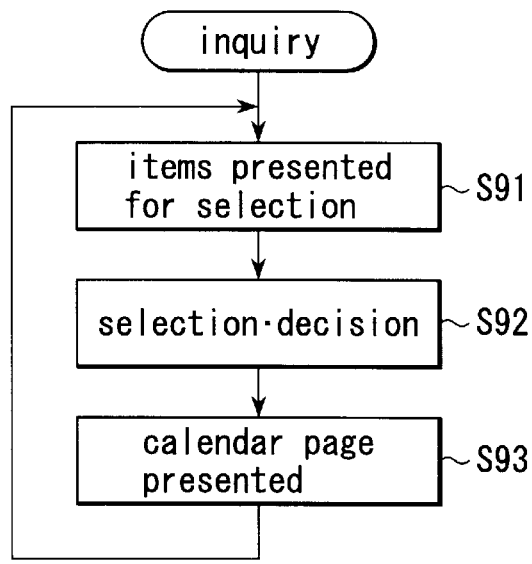
FIG. 21 is a flow chart showing the proceeding by which an inquiry is made.
Figure 22:
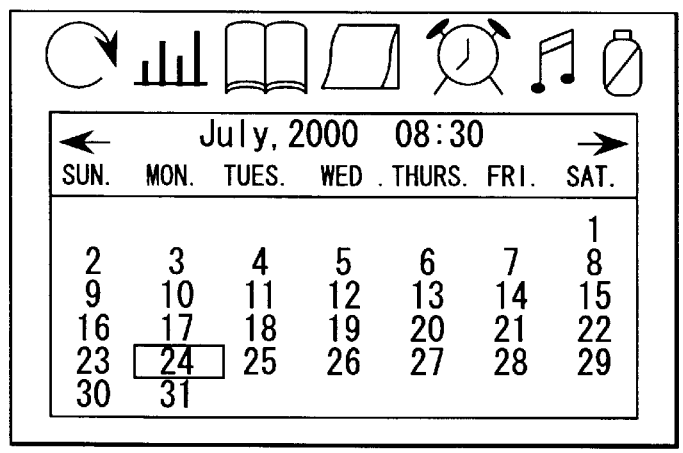
FIG. 22 is the initial image appearing in the display.
Figures 41, 42:
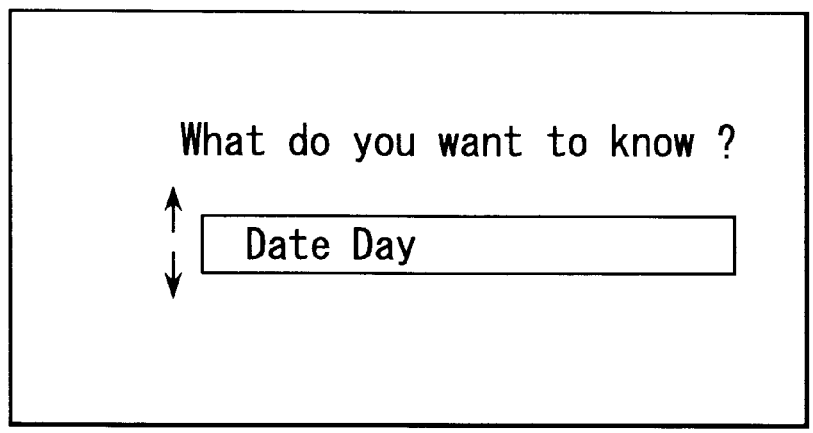
FIG. 41 shows an inquiry making screen.
FIG. 42 shows which days are Date Days.

Referring to FIG. 21, an inquiry processing (STEP S54) is described. At STEP S91 a message which reads "What do you want to know?" appears along with some items to be selected, as shown in FIG. 41. At STEP S92 the woman pushes the ↑ button sector or the ↓ button sector to scroll, and then the decision making button 41f is depressed. Examples of the items to be selected are: "Date Day", "Abnormal Bleeding Day", "Beginning Day of Menstruation Period", "Beginning Day of Next Menstruation Period", "Ovulation Day and Expected Date of Becoming Pregnant", "Expected Day of Next PMS", "Suitable Day of Dieting" and such like.

"Suitable Day (Period) of Dieting" can be determined as follows: the "Period" starts three days earlier than the expected Ovulation Day. Assuming that the woman's menstruation cycle has 28 days. The "Period" starts three days earlier than the fourteenth day from the day the menstruation is depressed. As a matter of course the start of the "Period" depends on the average menstruation cycle of the woman in question.

The swell disappears before the ovulation day, and the woman grows slim more or less while the body temperature has not risen yet. It is said that while the woman's body remains in such condition, the dieting can be effectively performed by taking care of food and exercise.

Termination of the "Period" is determined as follows: the BI curve descends to level off. The "Period" terminates on the fourth day counted forward from the beginning of the leveling-off period. Stated otherwise, the "Suitable Day of Dieting (Period)" terminates on the fourth day from the rise of the body temperature. The reason is that the consumption of energy increases while the body temperature remains at a high level.

Figure 11:
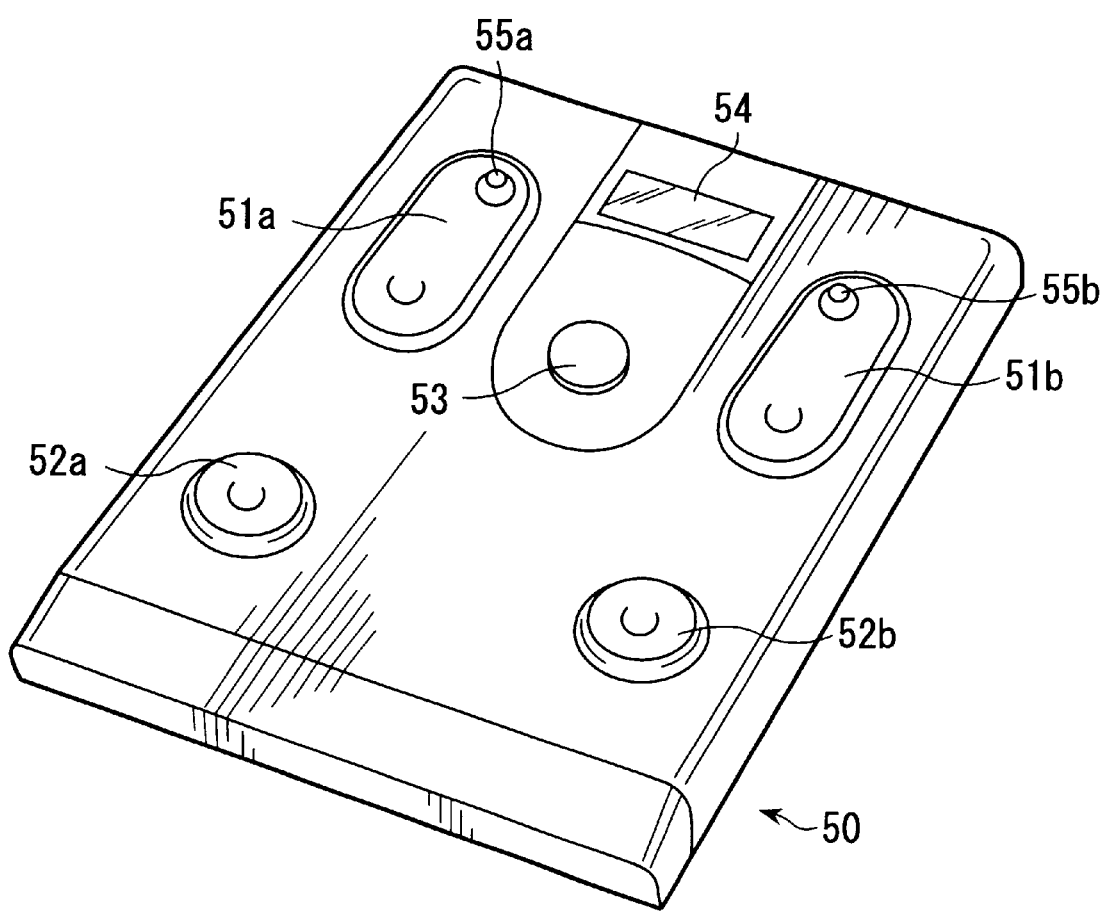
FIG. 11 is a perspective view of a female physical condition managing apparatus according to a second embodiment of the present invention.

At STEP S93 there appears the calendar page containing the day selected at STEP S92, which day blinks. Alternatively only the selected date may be displayed with character. Depression of the → button sector makes the proceeding return to STEP S91. Otherwise, if a predetermined length of time has passed, the proceeding returns to STEP S91. Depression of the cancel button 41h makes the proceeding return to STEP S3. Referring to FIG. 11, a female physical condition managing apparatus 50 according to the second embodiment has a scale-and-bioelectrical impedance meter and a control box both combined as a whole, and is capable of measuring the body temperature of the user. In these respects the apparatus 50 can be distinguished from the first embodiment of FIG. 9. The female physical condition managing apparatus 50 has constant current feeding electrodes 51a and 51b, voltage measuring electrodes 52a and 52b, an operating push button 53 and a display 54 arranged on its front. Body temperature measuring sensors 55a and 55b are placed at the upper parts of the constant current feeding electrodes 51a and 51b. These sensors 55a and 55b are so constructed that they may be pinched between selected fingers of both feet. Alternatively an ear measuring type of infrared thermometer may be connected to the female physical condition managing apparatus 50. A sublingual type of thermometer may be connected for precision measurement. The body temperatures thus measured can be used along with BI values for the CPU to make a decision on the women's monthly physical condition. Therefore, precision decision of the physical condition can be performed.

The female physical condition managing apparatus according to the first and second embodiments are so constructed that BI appealing between both hands or between one hand and one foot may be measured.

A selection button may be provided for selecting individual personal data among those stored in the memory, so that the apparatus may be used by two or more women in common.

It may be possible that the percent fat be determined from the measured BI values, and that the so determined percent fat be given in the display. On the basis of the body temperature and weight thus determined a decision can be made on the woman's periodic physical condition. These data may be given in the display.

Figure 43:
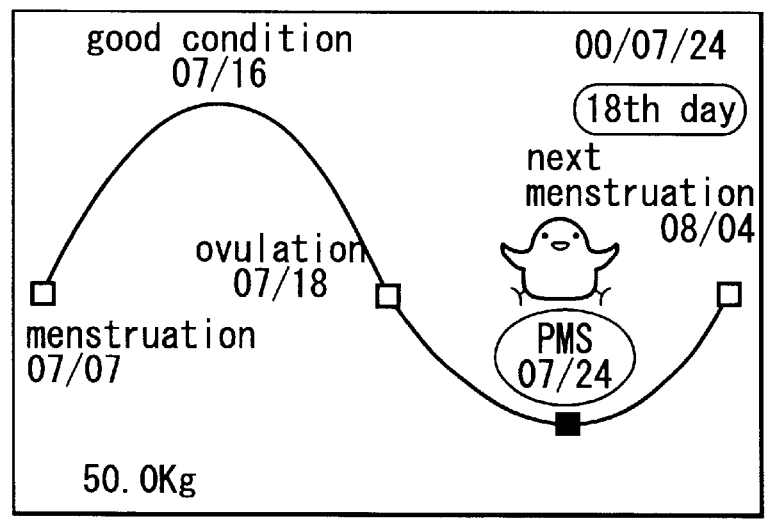
FIG. 43 illustrates the practice of the decisions being given in the display.

Referring to FIG. 43, the display of FIG. 27 is modified as shown in FIG. 43 according to another embodiment. The circular mark ○ stays on the day in question, blinking and encircling a message describing the present day's physical condition, as is in FIG. 27. In this particular embodiment the physical conditions on other specified days are shown along with the dates. Examples of such physical conditions are menstruation, "good condition" period, ovulation and next menstruation. A chick appears on the position at which the present day's physical condition is described. The weight appears on the lower, left side.

Figure 44:
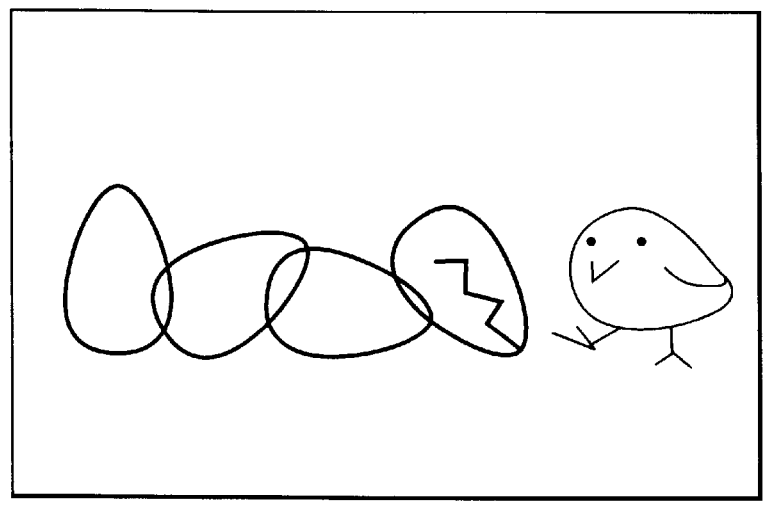
FIG. 44 illustrates animation-like figures appearing in the display while a required measurement is being made.

Referring to FIG. 44, the display of FIG. 26 is modified as shown according to still another embodiment. While measuring and making a decision on a selected subject an egg is rolling rightward, and the egg break. A chick appears from the broken egg just before termination of the decision-making. This animation may be replaced by a monthly incidence such as the transition from the crescent to full moon.

As may be understood from the above, a female physical condition managing apparatus according to the present invention shows the swell, feeling, body condition, skin condition, pheromone and such like in the form of line graph, thereby permitting women to realize the mental and physical conditions of the present day instantly.

What is claimed is:

1. A female physical condition managing apparatus comprising:
    an input unit which receives a menstruation beginning day;
    a plurality of pairs of electrodes which can be applied to selected points of an outer layer of the skin of a female;
    a bioelectrical impedance-meter which determines the value of bioelectrical impedance appearing between one of said pairs of electrodes;
    a memory for storing the so determined values of bioelectrical impedance; and
    a decision-making unit which regards the menstruation beginning day as a beginning day of a menstruation period, and determines a beginning day of a good condition period and a steady period based on the determined values of bioelectrical impedance and the menstruation beginning day, and indicates a level of feeling, a body condition level, a skin condition level and a pheromone level in the menstruation period, good condition period, and steady period in terms of the number of days counted from the beginning day of each period.

2. A female physical condition managing apparatus according to claim 1 wherein the body condition level includes a level of lassitude.

3. A female physical condition managing apparatus according to claim 2, further comprising: a display showing at least one of the level of feeling, the body condition level, the skin condition level and the pheromone level in the form of graphs.

4. A female physical condition managing apparatus according to claim 3 wherein the graphs include at least one of bar graphs, circle graphs, line graphs and radar charts.

5. A female physical condition managing apparatus according to claim 4 wherein the bar graphs, circle graphs, line graphs and radar charts are given in two or three dimensional form.

6. A female physical condition managing apparatus according to claim 1, further comprising: a display showing at least one of the level of feeling, the body condition level, the skin condition level, and the pheromone level in the form of graphs.

7. A female physical condition managing apparatus according to claim 6 wherein the graphs include at least one of bar graphs, circle graphs, line graphs and radar charts.

8. A female physical condition managing apparatus according to claim 7 wherein the bar graphs, circle graphs, line graphs and radar charts are given in two or three dimensional form.

* * * * *